US012097269B2

(12) United States Patent
Kundra et al.

(10) Patent No.: US 12,097,269 B2
(45) Date of Patent: Sep. 24, 2024

(54) DUAL MODE GADOLINIUM NANOPARTICLE CONTRAST AGENTS

(76) Inventors: Vikas Kundra, Missouri City, TX (US); James A. Bankson, Pearland, TX (US); Ananth Annapragada, Manvel, TX (US); Ketan B. Ghaghada, Houston, TX (US); Murali K. Ravoori, Pearland, TX (US)

(*) Notice: Subject to any disclaimer, the term of this patent is extended or adjusted under 35 U.S.C. 154(b) by 1168 days.

(21) Appl. No.: 13/283,272

(22) Filed: Oct. 27, 2011

(65) Prior Publication Data

US 2015/0283272 A1    Oct. 8, 2015

Related U.S. Application Data

(60) Provisional application No. 61/407,330, filed on Oct. 27, 2010.

(51) Int. Cl.
*A61K 49/18* (2006.01)
*A61K 31/704* (2006.01)
*A61K 49/14* (2006.01)

(52) U.S. Cl.
CPC ........ *A61K 49/1812* (2013.01); *A61K 31/704* (2013.01); *A61K 49/14* (2013.01)

(58) Field of Classification Search
CPC .............. A61K 49/085; A61K 49/1809; A61K 49/1812
See application file for complete search history.

(56) References Cited

U.S. PATENT DOCUMENTS

| | | | | |
|---|---|---|---|---|
| 6,090,408 | A * | 7/2000 | Li | A61K 49/1812 424/1.49 |
| 6,217,849 | B1 * | 4/2001 | Tournier | A61K 49/0466 424/9.321 |
| 6,869,591 | B2 * | 3/2005 | Lanza et al. | 424/9.32 |
| 2007/0292354 | A1 * | 12/2007 | Port | 424/9.321 |
| 2010/0158817 | A1 * | 6/2010 | Fossheim | A61K 49/1812 424/9.321 |
| 2010/0254913 | A1 * | 10/2010 | Burdinski et al. | 424/9.321 |
| 2011/0002977 | A1 * | 1/2011 | Li | A61K 31/136 424/450 |
| 2011/0200534 | A1 * | 8/2011 | Cheon et al. | 424/9.32 |

OTHER PUBLICATIONS

Terreno et al., Chem. Eur. J., 2009, 15, p. 1440-1448.*
Mulder, Mag. Res. Med., 2006, 55, p. 1170-4.*
Van Tilborg et al., Bioconjugate Chem., 2006, 17, 741-749.*
Laurent et al., Langmuir 2008, 24, 4347-4351.*
De Cuyper et al., Analytical Biochemistry, 2007, 367, p. 266-273.*
Kim et al., J. Magnetism and Magnetic Materials, 2005, 289, p. 328-330.*
Strijkers et al., Magma, 2005, 18, p. 186-192. (Year: 2005).*
Glogard et al., Int. J. Pharmaceutics, 2002, 233, p. 131-140. (Year: 2002).*
Mulder et al., Bioconjugate Chem., 2004, 15, p. 799-806. (Year: 2004).*
Jackson et al., Lyotropic liposomes toward MRI/fluorescence localization and thermal ablation of tumors, 21st International Liquid Crystal Conf., 2006. (Year: 2006).*
Anzalone, et al., "High relaxivity contrast agents in MR angiography of the carotid arteries," *Eur. Radiol.*, 16(Suppl. 7):M27-34, 2006.
Ayyagari, et al., "Long-circulating liposomal contrast agents for magnetic resonance imaging," *Magn. Reson. Med.*, 55:1023-9, 2006.
Bremerich, et al., "MR angiography with blood pool contrast agents," *Eur. Radiol.*, 17:3017-24, 2007.
Bucholz, et al., "Four-dimensional MR microscopy of the mouse heart using radial acquisition and liposomal gadolinium contrast agent," *Magn. Reson. Med.*, 60:111-8, 2008.
Choyke, et al., "Functional tumor imaging with dynamic contrast-enhanced magnetic resonance imaging," *J. Magn. Reson. Imaging*, 17:509-20, 2003.
Eckelman, "The use of PET and knockout mice in the drug discovery process," *Drug Discov. Today*, 8:404-10, 2003.
Ferrari, "Cancer nanotechnology: opportunities and challenges," *Nat. Rev. Cancer*, 5:161-71, 2005.
Frias, et al., "Recombinant HDL-like nanoparticles: a specific contrast agent for MRI of atherosclerotic plaques," *J. Am. Chem. Soc.*, 126:16316-7, 2004.
Gabizon, et al., "Pharmacokinetics of pegylated liposomal Doxorubicin: review of animal and human studies," *Clin. Pharmacokinet.*, 42:419-36, 2003.
Ghaghada, et al., "New dual mode gadolinium nanoparticle contrast agent for magnetic resonance imaging," *PLoS One*, 4:e7628, 2009.
Ghaghada, et al., "High-resolution vascular imaging of the rat spine using liposomal blood pool MR agent," *AJNR Am. J. Neuroradiol.*, 28:48-53, 2007.
Ghaghada, et al., "T1 relaxivity of core-encapsulated gadolinium liposomal contrast agents—effect of liposome size and internal gadolinium concentration," *Acad. Radiol.*, 15:1259-63, 2008.
Gupta and Gupta, "Synthesis and surface engineering of iron oxide nanoparticles for biomedical applications," *Biomaterials*, 26:3995-4021, 2005.
Hadizadeh, et al., "Peripheral MR angiography with blood pool contrast agent: prospective intraindividual comparative study of high-spatial-resolution steady-state MR angiography versus standard-resolution first-pass MR angiography and DSA," *Radiology*, 249:701-11, 2008.

(Continued)

*Primary Examiner* — Michael G. Hartley
*Assistant Examiner* — Leah H Schlientz
(74) *Attorney, Agent, or Firm* — Parker Highlander PLLC

(57) ABSTRACT

Provided herein are nanoparticle-based gadolinium (Gd) agents which may be used, e.g., in T1-weighted MR imaging (MRI). In various embodiments, dual-Gd liposomal agents are provided which contain both core-encapsulated Gd as well as surface-conjugated Gd. In various embodiments, these agents were observed to deliver a higher concentrations of Gd and result in substantial improvements in signal to noise ratios and contrast to noise ratios. Also provided are methods for in vivo imaging and/or treating diseases such as cancer or tumor in a subject.

33 Claims, 5 Drawing Sheets

(56) References Cited

OTHER PUBLICATIONS

Ishida, et al., "Size-dependent extravasation and interstitial localization of polyethyleneglycol liposomes in solid tumor-bearing mice," *Int. J. Pharm.*, 190:49-56, 1999.

Kamaly and Miller, "Paramagnetic liposome nanoparticles for cellular and tumour imaging," *Int. J. Mol. Sci.*, 11:1759-76, 2010.

Karathanasis, et al., "Tumor vascular permeability to a nanoprobe correlates to tumor-specific expression levels of angiogenic markers," *PLoS One*, 4:e5843, 2009.

Knopp, et al., "Contrast-enhanced MR angiography of the run-off vasculature: intraindividual comparison of gadobenate dimeglumine with gadopentetate dimeglumine," *J. Magn. Reson. Imaging*, 17:694-702, 2003.

Kobayashi and Brechbiel, "Nano-sized MRI contrast agents with dendrimer cores," *Adv. Drug. Deliv. Rev.*, 57:2271-86, 2005.

Mulder, et al., "A liposomal system for contrast-enhanced magnetic resonance imaging of molecular targets," *Bioconjug. Chem.*, 15:799-806, 2004.

Port, et al., "How to compare the efficiency of albumin-bound and nonalbumin-bound contrast agents in vivo: the concept of dynamic relaxivity," *Invest. Radiol.*, 40:565-73, 2005.

Rosen and Schnall, "Dynamic contrast-enhanced magnetic resonance imaging for assessing tumor vascularity and vascular effects of targeted therapies in renal cell carcinoma," *Clin. Cancer Res.*, 13:770s-776s, 2007.

Scheinin, et al., "PET in drug discovery and development: an introduction," *Ann. Med.*, 31:430-1, 1999.

Storrs, et al., "Paramagnetic polymerized liposomes as new recirculating MR contrast agents," *J. Magn. Reson. Imaging*, 5:719-24, 1995.

Strijkers, et al., "Relaxivity of liposomal paramagnetic MRI contrast agents," *MAGMA*, 18:186-92, 2005.

Terreno, et al., "Effect of the intracellular localization of a Gd-based imaging probe on the relaxation enhancement of water protons," *Magn. Reson. Med.*, 55:491-7, 2006.

Tilcock, et al., "Liposomal Gd-DTPA: preparation and characterization of relaxivity," *Radiology*, 171:77-80, 1989.

Tran, et al., "Clinical applications of perfluorocarbon nanoparticles for molecular imaging and targeted therapeutics," *Int. J. Nanomedicine*, 2:515-26, 2007.

Welch, et al., "The advantages of nanoparticles for PET," *J. Nucl. Med.*, 50:1743-6, 2009.

Winter, et al., "Improved molecular imaging contrast agent for detection of human thrombus," *Magn. Reson. Med.*, 50:411-6, 2003.

Zhang, et al., "3D contrast-enhanced MR angiography," *J. Magn. Reson. Imaging*, 25:13-25, 2007.

Ravoori et al., "Multimodal magnetic resonance and near-infrared-fluorescent imaging of intraperitoneal ovarian cancer using a dual-mode-dual-gadolinium liposomal contrast agent," *Scientific Reports*, 6:38991, 2016.

\* cited by examiner

FIGS. 6A-B
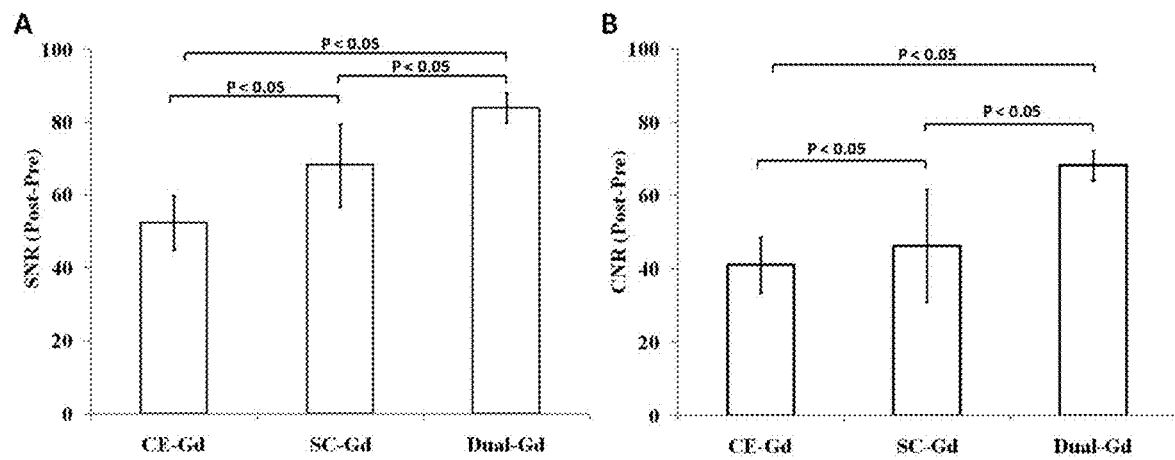
FIG. 7
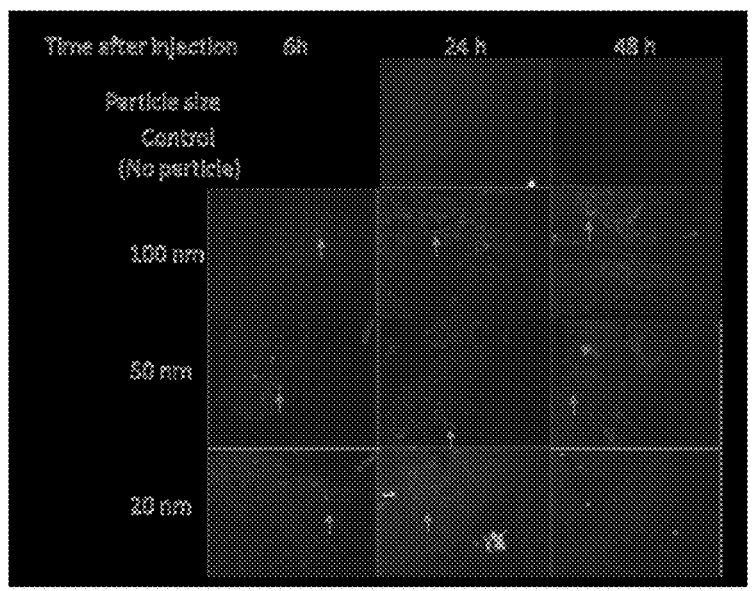

FIGS. 8A-D
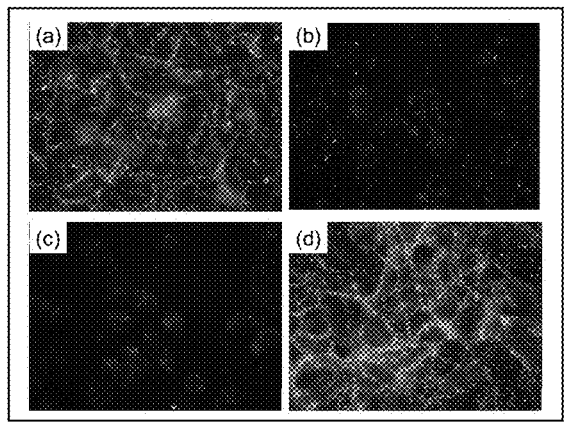
FIG. 9
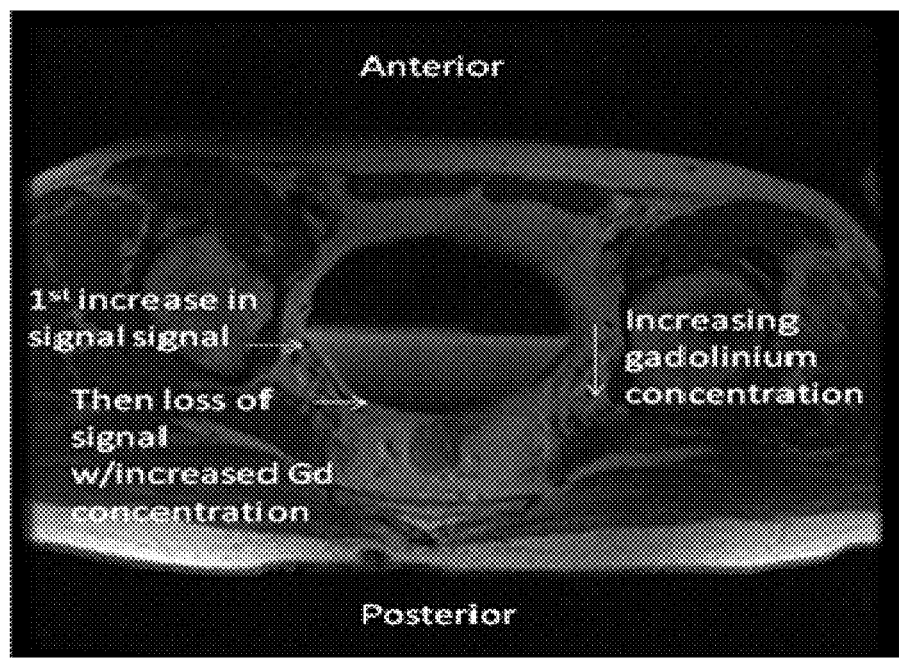

DUAL MODE GADOLINIUM NANOPARTICLE CONTRAST AGENTS

This application claims priority to U.S. Application No. 61/407,330 filed on Oct. 27, 2010, the entire disclosure of which is specifically incorporated herein by reference in its entirety without disclaimer.

This invention was made with government support under W81XWH-06-2-0067 awarded by the Alliance of Nanohealth via the United States of Department of Defense. The government has certain rights in the invention.

BACKGROUND OF THE INVENTION

1. Field of the Invention

The present invention relates generally to the fields of molecular biology and medicine. More particularly, it concerns contrast agents for imaging using, e.g., magnetic resonance imaging (MRI).

2. Description of Related Art

T1-based MR contrast agents, exemplified by conventional low molecular-weight Gd-chelates have enabled contrast enhanced MRI for various applications such as tumor detection and characterization as well as vascular imaging (Zhang et al., 2007; Choyke et al., 2003; Rosen and Schnall, 2007). For both of these applications, the T1 relaxivity of the agent can affect detection and anatomic demarcation of normal anatomy as well as pathology by reducing the T1 relaxation rate of tissue and generating positive contrast in T1-weighted images. This is valuable for imaging normal anatomy and for functional/targeted imaging; both have been limited by the amount of contrast generated by MR imaging agents. In contrast-enhanced MR angiography (CE-MRA), conventional low molecular weight contrast agents extravasate into the extravascular-extracellular compartment (EEC) rather quickly, leaving a short window for imaging the vessel lumen. This can lead to blurring of the resulting images and low vessel conspicuity, particularly for smaller vessels. The problem is further exacerbated if the bolus is not appropriately timed, which can severely limit imaging of both large and small vessels. One approach to circumventing the need for accurate bolus timing involves the use of agents with longer intravascular half-life (Bremerich et al., 2007; Hadizadeh et al., 2008). Slowerl extravasation reduces blurring at vessel boundaries and increases the contrast-to-noise (CNR) ratio between vascular structures and surrounding tissues. In addition, an agent with high T1 relaxivity can also improve imaging of small features by increasing the amount of signal generated within the vascular space in CE-MRA (Knopp et al., 2003; Anzalone et al., 2006).

The T1 relaxivity and in vivo half-life of a contrast agent becomes even more critical in small animal imaging, where the vessels are much smaller than in humans, resulting in longer scan times and therefore increased propensity to extravasate into the extravascular space. In recent work, this shortcoming was highlighted in small animal imaging (Ghaghada et al., 2007), where even under optimized imaging conditions in a 7 T scanner, it was not possible to clearly image the intercostal and spinal vasculature in a rat with conventional low molecular-weight Gd-chelates. Thus, agents that remain intravascular and have greater T1-relaxivity per unit of contrast agent are needed in order to amplify signal, improve CNR, and enable vascular imaging with high vessel conspicuity. In oncology, such agents may be used for evaluating enhanced permeability and retention of tumors and may be used to image vascular targets that may be pathologic or normal or lesions that do not have intact vasculature such as tumors. Such agents may also be used for vascular targets. Smaller sized such agents that escape the vasculature may also be used for extra-vascular targets. Thus, such agents should have applications for cellular and molecular imaging.

Previous attempts to produce concentration of multiple T1 shortening agents such as Gd has resulted in significant loss of signal (Terreno et al., 2006; Kamaly and Miller, 2010). There is clearly a need in the art for improved imaging agents.

SUMMARY OF THE INVENTION

The present invention overcomes limitations in the prior art by providing improved imaging agents which may be used, e.g., in T1-weighted MR imaging (MRI). In particular, it has been discovered that nanoparticle-based gadolinium (Gd) agents which contain both core-encapsulated Gd as well as surface-conjugated Gd ("dual-Gd" agents) can exhibit substantial advantages over previously-used imaging agents. In contrast to previous reports that multiple loading of Gd in a nanoparticle can result in substantial loss of signal, dual-Gd liposomal agents provided herein were observed to exhibit substantial improvements over previously used imaging agents including: improved delivery of higher concentrations of Gd, improved signal enhancement per particle signal to noise ratios (SNR), improved contrast to noise ratios (CNR), and improved nanoparticle-based T1 relaxivity.

Nanotechnology is an applied science that creates and studies molecules or aggregates that have an overall size in the 1-1000 nm range (<1 μm). In the last few years, nanoparticles have been used in biomedical studies investigating new and improved diagnosis and therapy agents. Oncology is one of the disciplines that has benefited most from nanotechnology. Radioisotopes linked to nanoparticles through a chelating agent may also be used in non-invasive nuclear imaging. Among other applications, dual-Gd agents may be used for vascular imaging, particularly for evaluation of small features that may be critical for clinical decision making and/or for imaging of small animals. Additionally, dual-Gd agents may be used for molecular imaging, where the number of imaging agents per particle bound to the target is critical for creating sufficient signal for target identification.

An aspect of the present invention relates to an imaging nanoparticle comprising a liposome or micelle, wherein the liposome or micelle comprises both a first magnetic resonance imaging agent on the surface of the liposome or micelle and a second magnetic resonance imaging agent that is inside or substantially encapsulated within the liposome or micelle. The first and second imaging agents may each be a T1-shortening agent or a T2-shortening agent. In some embodiments, the first and second imaging agents are T1-shortening agents. The T1-shortening agents may comprise a lanthanide, such as a chelated lanthanide. The lanthanide may be gadolinium. In some embodiments, both the first and second imaging agents each comprise a chelated gadolinium contrast agent. The first and second imaging agents may each independently be selected from the group consisting of Gd-DTPA bis(stearylamide), gadodiamide, gadobenic acid, gadobenate dimeglumine, gadopentetic acid, gadopentetate dimeglumine, gadoteridol, gadofosveset, gadoversetamide, gadoxetic acid, gadobutrol, gadoteric acid, gadoxetic acid disodium, gadobutrol, gadocoletic acid, gadodenterate, gadomelitol, and gadopenamide. In some embodiments, the first imaging agent is Gd-DTPA bis (stearylamide) and the second imaging agent is gadobenate dimeglumine. The first imaging agent may be a surface-conjugated imaging agent. The first imaging agent may comprise a chelated gadolinium that is covalently bound to a surface moiety, wherein the surface moiety is associated with a the surface of the nanoparticle. The chelated gadolinium may comprise DTPA-Gd. The surface moiety may comprise a surface stabilizer. The surface stabilizer may be selected from the group consisting of citrate, cysteine, folic acid, polyacetylene glycol, polypropylene glycol, copolymers of polyethylene glycol and polypropylene glycol, polylysine, polyvinyl alcohol, human serum albumin, bovine serum albumin, hyaluranic acid, polyethyleimine (PEI), polyvinylprrolidone (PVP), and polyethylene glycol (PEG). In some embodiments, the surface moiety is bis (stearylamide). The first and second imaging agents may comprise chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) erbium (III), lanthanum (III), gold (III), lead (II), and/or bismuth (III). The liposome or micelle may be further defined as a nanoparticle contrast agent. In some embodiments, the nanoparticle comprises a PEGylated or stealth liposome. The nanoparticle may comprise a PEGylated or stealth micelle. The nanoparticle may comprise a cleavable liposome or a cleavable micelle. The nanoparticle may comprise a cleavable stealth liposome or a cleavable stealth micelle. The nanoparticle may comprise 1,2-dipalmitoyl-sn-glycero-3-phosphocholine (DPPC), cholesterol, and/or 1,2-distearoyl-sn-glycero-3-phosphoethanolamine-N-[methoxy(poly(ethylene glycol))-2000] (mPEG2000-DSPE). The nanoparticle may further comprise a radioisotope, such as, e.g., astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$, yttrium$^{90}$, leutitium. The nanoparticle may further comprise an imaging agent that is detectable via radiography, CT, ultrasound, planar gamma camera imaging, SPECT, PET, other nuclear medicine-based imaging, optical imaging using visible light, optical imaging using luciferase, optical imaging using a fluorophore, other optical imaging, imaging using near infrared light, or imaging using infrared light. The nanoparticle may further comprise a light-based imaging agent, a nuclear medicine imaging agent, a CT imaging agent, an ultrasound imaging agent, or a photoacoustic imaging agent.

In some embodiments, the nanoparticle further comprises a chemotherapeutic, such as doxorubicin, an RNA, an siRNA, or a gene therapy. The nanoparticle may comprise a therapeutic agent, such as an Alzheimer's therapeutic, an anti-infection agent, or an antimicrobial agent. The nanoparticle may further comprise a surface stabilizer. The surface stabilizer may comprise citrate, cysteine, folic acid, polyacetylene glycol, polypropylene glycol, copolymers of polyethylene glycol and polypropylene glycol, polylysine, polyvinyl alcohol, human serum albumin, bovine serum albumin, hyaluranic acid, polyethyleimine (PEI), or polyvinylprrolidone (PVP). The polyacetylene glycol may be a polyethylene glycol (PEG). The polyethylene glycol may have a molecular weight ranging from about 500-20,000 dalton, about 1000-5000 dalton. The nanoparticle may have a diameter or an average diameter of about 1 nm to 250 nm, more than about 10 nm, less than 150 nm, or about 10-125 nm. The nanoparticle may comprise a third imaging agent, such as a near-infrared absorption imaging agent or a fluorescent imaging agent. In some embodiments, the second imaging agent is a near-infrared absorption imaging agent, wherein the near-infrared absorption imaging agent has a maximum absorption at about 700 to 1100 nm. The near-infrared absorption imaging agent may be selected from the list consisting of FITC, rhodamine, Cy5.5, and, an Alexa dye. The third imaging agent may be a fluorescent imaging agent such as, e.g., carboxyfluorescein, rhodamine, or an Alexa dye. The nanoparticle may be further coupled with a targeting moiety, a tumor targeting moiety, a targeting ligand, a therapeutic, a peptide, an antibody, a nucleic acid, a small molecule, or a polymer. The targeting ligand may bind to CD44 or folate receptors. The targeting ligand may comprise hyaluronic acid (HA) or folic acid. In some embodiments, the tumor targeting moiety targets a somatostatin receptor, such as somatostatin receptor type 2. The tumor targeting moiety may comprise octreotide.

Another aspect of the present invention relates to a method of imaging a subject comprising administering a nanoparticle of the present invention to a subject. The administering may comprise intravenous administration, intracardiac administration, intradermal administration, intralesional administration, intrathecal administration, intracranial administration, intrapericardial administration, intraumbilical administration, intraocular administration, intraarterial administration, intraperitoneal administration, intraosseous administration, intrahemmorhage administration, intratrauma administration, intratumor administration, subcutaneous administration, intramuscular administration, intravitreous administration, direct injection into a normal tissue, or direct injection into a tumor. The method may further comprise imaging a tumor in the subject. The tumor may be a neuroendocrine tumor, breast tumor, lung tumor, prostate tumor, ovarian tumor, brain tumor, liver tumor, cervical tumor, colon tumor, renal tumor, skin tumor, head and neck tumor, bone tumor, esophageal tumor, bladder tumor, uterine tumor, lymphatic tumor, stomach tumor, pancreatic tumor, testicular tumor, or lymphoma. The method may further comprise a method of imaging atherosclerosis or an atherosclerotic plaque. The method may further comprise a method of imaging a stenosis, renal artery stenosis, carotid artery stenosis, or a coronary artery stenosis, other cellular target such as a particular cell type or group of neurons in the nervous system (e.g., dopaminergic neurons, etc.), a neurodegerative disease, a genetic disease, a traumatic disease, a target of drug addiction, a vascular diseases such as atherosclerosis, a neoplasm, a delivered gene product or cells which may be delivered therapeutically to a subject, such as a mammal, such as a mouse, a rat, rabbit, pig, dog, monkey, ape, or a human.

Yet another aspect of the present invention relates to a method of imaging and treating an angiogenic or a malignant tissue in a subject, comprising administering to a subject an effective amount of a nanoparticle of the present invention to a subject, wherein the nanoparticle further comprises a therapeutic agent. The therapeutic agent may be an anticancer agent, such as a chemotherapeutic (e.g., doxorubicin), radioisotope, therapeutic RNA, an siRNA, or a gene therapy. The subject may be a mammal, such as a human.

Another aspect of the present invention relates to a method of making a nanoparticle of the present invention, comprising: (a) forming a first solution, wherein the solution comprises a lipid mixture and the first magnetic resonance imaging agent compound; (b) evaporating at least a portion of the first solution; and (c) re-hydrating and mixing the lipid mixture with a second solution comprising the second magnetic resonance imaging agent compound. The first imaging agent and the second imaging agent may each be a chelated gadolinium compound. The first solution may comprise a polyethylene glycol (PEG). In some embodiments, the first solution comprises DPPC, cholesterol and mPEG2000-DSPE. The first chelated gadolinium compound may be Gd-DTPA-bis(stearylamide) (Gd-DTPA-BSA). In some embodiments, DPPC, Gd-DTPA-BSA, cholesterol and mPEG2000-DSPE are in the molar ratio of about 30:25:40:5. The mPEG may be covalently bound to a targeting moiety. The first solution may comprise chloroform and methanol. Step (b) may comprise evaporating the first solution substantially to dryness. The second solution may comprise gadodiamide, gadobenic acid, gadobenate dimeglumine, gadopentetic acid, gadopentetate dimeglumine, gadoteridol, gadofosveset, gadoversetamide, gadoxetic acid, gadobutrol, gadoteric acid, gadoxetic acid disodium, gadobutrol, gadocoletic acid, gadodenterate, gadomelitol, or gadopenamide. The second solution may comprise gadobenate dimeglumine or Gd-BOPTA. The method may further comprise extruding or filtering the rehydrated mixture through a filter or membrane. The filter or membrane has a plurality of openings about 1-500, 100-400, 1-2, 1-5, 5-10, 10-15, 15-20, 20-25, 25-30, 30-40, 40-50, 50-60, 60-70, 70-80, 80-90, 90-100, 50-75, 75-100, 100-125, 125-150, 100-150, 100-200, 150-200, 200-300, 300-400, or 200-500 nm in size. The filtered rehydrated mixture may be comprised in a pharmaceutical composition.

Certain aspects of the present invention are based on a hypothesis that the full capability of liposomes to amplify signal has not been exploited and it was therefore tested whether liposomes that both encapsulate and display gadolinium on their surface would exhibit increased T1 relaxivity in vitro and whether this leads to further signal enhancement in vivo. As described below, CE-Gd (Core-Encapsulated) nanoparticles that encapsulated gadolinium within the core-interior, SC-Gd (Surface-Conjugated) nanoparticles that have gadolinium conjugated on the surface, and Dual-Gd for particles that have both core-encapsulated and surface-conjugated gadolinium were generated and evaluated (see, e.g., FIG. 1).

Three types of liposomal agents were fabricated: core-encapsulated, surface-conjugated and dual-mode gadolinium liposomes. In vitro physico-chemical characterizations of the agents were performed to determine particle size and elemental composition. Gadolinium-based and nanoparticle-based T1 relaxivities of various agents were determined in bovine plasma. Subsequently, the agents were tested in vivo for contrast-enhanced magnetic resonance angiography (CE-MRA) studies. Characterization of the agents demonstrated the highest gadolinium atoms per nanoparticle for Dual-Gd liposomes. In vitro, surface-conjugated gadolinium liposomes demonstrated the highest T1 relaxivity on a gadolinium-basis. However, Dual-Gd liposomes demonstrated the highest T1 relaxivity on a nanoparticle-basis. In vivo, Dual-Gd liposomes resulted in the highest signal-to-noise ratio (SNR) and contrast-to-noise ratio.

As described in the below examples, the dual-mode gadolinium liposomal contrast agent demonstrated higher particle-based T1 relaxivity, both in vitro and in vivo, compared to either the core-encapsulated or the surface-conjugated liposomal agent. The dual-mode gadolinium liposomes could enable reduced particle dose for use in CE-MRA and increased contrast sensitivity for use in molecular imaging.

As used herein, "fluorophore" refers to a molecule or part of a larger molecule, which, when irradiated with light having a wavelength corresponding at least in part to the absorption band(s) of the fluorophore, absorbs part or all of the light energy then emits light at a different (longer or shorter) wavelength in the form of fluorescence. Fluorophore molecules are well-known in the art and include lead compounds, fluoresceins, rhodamines, tryptamines, acrydines, coumarins, actinomycins, fuchsins, acriflavins, alexa fluor(s)™, alizarins, aminomethylcoumarin, aminoactinomycin, allophycocyanin, APC-Cy7, Bodipy(s)™, Cy5.18, cy5.5, cy5, cy7, dabsyl, dansyl, DiR, DY-630-NHS, DY-635-NHS, DY780, DY880, DY885, FM 1-43™, FM 4-46, Fura Red™ (high pH), Indodicarbocyanine (DiD), Indotricarbocyanine (DiR), LaserPro, SYTO, chlorines, chlorophylls, cyanines, fullerenes, metallophthalocyanines, metalloporphyrins, methylenporphyrins, naphthalimides, naphthalocyanines, nile blue, perylenequinones, phenols, pheophorbides, pheophyrins, phthalocyanines, porphycenes, porphyrins, psoralens, purpurins, quinines, retinols, thiophenes, verdins, xanthenes, and dimers and oligomers thereof. Fluorophores also includes fluorophore derivatives; for example, the positions in a fluorophore may be functionalized by an alkyl (e.g., a $C_1$-$C_{25}$ alkyl or a $C_1$-$C_{12}$ alkyl), functional group, peptide, protein, or nucleic acid or a combination thereof.

Non-limiting examples of paramagnetic ions of potential use as imaging agents include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), and gadolinium may be particularly useful in certain embodiments. Some ions such as ytterbium can result in fluorescence. Ions useful in other contexts, such as X-ray imaging, include but are not limited to iodine, barium, lanthanum (III), gold (III), lead (II), and especially bismuth (III).

Radioisotopes of potential use as imaging or therapeutic agents include astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and yttrium$^{90}$, leutitium $^{125}$I is often being preferred for use in certain embodiments, and technicium$^{99m}$ and indium$^{111}$ are also often preferred due to their low energy and suitability for long range detection.

Nanoparticles may be used in an imaging or detection method for diagnosis or localization of tumor or angiogenic tissues. Any optical or nuclear imaging method may be contemplated, such as PET, SPECT, CT, or photoacoustic tomography in addition to MR. The integrated radioactive isotope in the nanoparticle may exert a radiotherapy on the tissue incorporating such nanoparticle. In addition, a photothermal ablation therapy may be administered to the tissue having the nanoparticle to enhance the therapeutic effect.

Metal nanoparticles may have any transition metal as an integral component, such as the core of nanoparticles. Transition metals in the nanoparticles are virtually insoluble in aqueous solutions due to partially covalent character of the crystal lattice. Non-limiting examples of transition metals in the nanoparticles include one or more of zinc, molybdenum, cadmium, scandium, titanium, vanadium, chromium, manganese, iron, cobalt, nickel, copper, yttrium, zirconium, niobium, technetium, ruthenium, rhodium, palladium, silver, hafnium, tantalum, tungsten, rhenium, osmium, iridium, platinum, gold, mercury, rutherfordium, dubnium, seaborgium, rohrium, hassium, meitnerium, darmstadtium, roentgenium, and copernicium.

In certain aspects, the nanoparticle may further comprise a surface stabilizer. Non-limiting examples of surface stabilizer include citrate, polyacetylene glycol, cysteine, folic acid, polypropylene glycol, copolymers of polyethylene glycol and polypropylene glycol, polylysine, polyvinyl alhocol, human serum albumin, bovine serum albumin, hyaluranic acid, polyethyleimine (PEI), polyvinylprrolidone (PVP) or any chemical compound that passivates the surface of nanoparticle and protects the nanoparticle from further growth. For example, the polyacetylene glycol is polyethylene glycol (PEG). The polyethylene glycol may have a molecular weight ranging from 500-20,000 dalton, or more particularly, from 1000-5000 dalton. For example, the PEG may have at least, at most or about 100, 200, 300, 400, 500, 600, 700,800, 900, 1000, 2000, 3000, 4000, 5000, 6000, 7000, 8000, 9000, 10,000, 20,000, 30,000, 40,000, 50,000 dalton, or any range derivable therefrom.

The surface stabilizer may be virtually composed of a monomolecular layer. The surface property of nanoparticles, particularly property of the surface stabilizer layer, could determine the solubility, chemical reactivity, biodistribution, or pharmacokinetic properties of nanoparticles. Very small size, uniformity of particles, and critical role of the surface distinguishes nanoparticles from both colloidal and molecular systems.

The term nanoparticle may be used to describe objects of from 1 to 300 nm in diameter represented by vesicles, polymers or colloids. These species are used for drug delivery and for diagnostic purposes. The nanoparticle may have a particle diameter of less than 1000 nm, about 10 nm to about 500 nm, about 10 to 200 nm, about 20 to about 200 nm, about 20 to about 100 nm, about 20 to about 30 nm, or any range derivable therein. The particle diameter may be a mean or an average diameter.

Confusion of terms used in different fields of chemistry should not obscure the fundamental difference that drug delivery agents are expected to remain in the blood stream for relatively long time while the radiolabeled agents must have a rapid blood clearance which is hardly achievable with large species 50-300 nm in diameter. Accordingly, it is contemplated that the term nanoparticles in certain aspects of the present invention includes particles of a smaller diameter. For example, the nanoparticle may have a diameter of at least, about, or at most, 1, 2, 3, 4, 5, 6, 7, 8, 9, 10, 11, 12, 13, 14, 15, 16, 17, 18, 19, 20, 25, 30, 31, 32, 33, 34, 35, 40, 45, 50, 55, 60, 65, 70, 75, 80, 85, 90, 95, 100, 150 or 200 nm, or any intermediate ranges. By choosing an appropriate stabilizer and reaction conditions, one can alter the diameter of the nanoparticle with a precision of a few Angstroms.

Phototheraml ablation (PTA) therapy has been used in minimally invasive treatments for cancer. Nanoparticles with optical properties such as infrared absorption may be used as photothermal coupling agents for PTA therapy to convert optical energy to thermal energy, enabling optical energy into tumors for thermal ablation. In certain aspects, the nanoparticle has a near-infrared absorption. For example, the nanoparticle has a maximum absorption at about, at least or at most 700, 750, 800, 850, 900, 950, 1000, 1100 nm or any intermediate range.

In a further aspect, the nanoparticle may be coupled with a targeting moiety, tumor targeting moiety, a targeting ligand, a therapeutic, an imaging agent, a peptide, an antibody, a nucleic acid, a small molecule, or a polymer. For example, the targeting ligand may be a CD44 targeting ligand, such as hyaluronic acid (HA), for selective targeting of nanoparticles to CD44 positive tumor cells. In a further aspect, the targeting ligand may bind to folate receptors, such as a targeting ligand comprising folic acid.

In certain aspects, the nanoparticle may be formulated in a pharmaceutically acceptable nanopartcile composition. The nanoparticle formulation can be a liquid formulation or a solid formulation, such as a powder. Particularly, the composition may be dehydrated or lyophilized for long term storage with improved stability. Alternatively, the composition may be present in a substantially aqueous solution. The composition may be rehydrated or re-suspended in a solution or liquid from the previously lyophilized composition. The composition used in the methods may be previously dehydrated, lyophilized or in some other aspects, an aqueous solution or liquid formulation of previously lyophilized or dehydrated composition, an effective amount of which are administered to the subject. The present invention also provides, in certain aspects, previously lyophilized or dried composition after being stored at 4 degree for at least 1 week, for at least 3 weeks, for up to 4 weeks, or any period derivable therein, for treating the disease with retained activity after resuspension or rehydration.

For imaging normal, pathologic, delivered, angiogenic or maligant cells and/or tissue, the method may comprise imaging the nanoparticles in the subject after a period of time that is sufficient for the nanoparticles to enter such cells/tissue.

The imaging may further comprise imaing of lymph nodes in the subject. For example, an imaging nanoparticle can be used for lymph node imaging with MR. This application can be potentially used in noninvasive detection of lymph node metastasis. The ability to detect lymph nodes metastasis is extremely important in cancer staging, determining prognosis, and monitoring treatment outcome.

The method may further comprise administering a photothermal ablation therapy to the tissue having the nanoparticles. The photothermal ablation therapy may comprise administering to the tissue a near-infrared light, for example, from a a near-infrared laser at about 8, 9, 10, 11, 12, 13, 14, 15, 16, 17, 18, 19, 20 W/cm2 or any intermediate range for about 0.5, 1, 2, 3, 4, 5, 6, 7, 8, 9, 10 minutes or any intermediate range. The near-infrared light may have a wavelength of about 700, 750, 800, 850, 900, 950, 1000, 1100 nm or any intermediate range.

The subject may be any animal, like a mammal. In particular, the subject may be a human or a mouse. The subject may have cancer. The cancer may include melanoma, leukemia, ovarian cancer, colon cancer, prostate cancer, lung cancer, liver cancer, pancreatic cancer, bladder cancer, breast cancer, ovarian cancer, gastric cancer, colon cancer, head and neck cancer, esophagus cancer, synovium cancer, brain cancer, bronchus cancer or any known cancer.

For a safe and effective dosage, the nanoparticle or nanoparticle formulation may be administered at a dose of at least, at most or about 1, $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $2\times10^{14}$, $3\times10^{14}$, $4\times10^{14}$, $5\times10^{14}$, $8\times10^{14}$, $1\times10^{15}$, $1\times10^{16}$, $1\times10^{17}$, $1\times10^{18}$, $1\times10^{19}$, $1\times10^{20}$ particles or any intermediate range per kg body weight or per tumor. The nanoparticle or nanoparticle formulation administered to the subject may have a radioactivity of at least, at most or about 0.001, 0.01, 0.1, 1, 10, 100, 1000 milliCi per kg body weight or per tumor, or any range deriable therein. In certain aspects, the nanoparticle or nanoparticle formulation may be administered about 500 mg/m2 (body surface)/day, about 10 to about 300 mg/m2/day, 20 to about 200 mg/m2/day, about 30 to about 200 mg/m2/day, about 40 to about 100 mg/m2/day, about 50 to about 100 mg/m2/day or any range derivable therein to a subject such as a human.

The nanoparticle or nanoparticle formulation may be administered intravenously, intradermally, intraarterially, intraperitoneally, intralesionally, intracranially, intraarticularly, intraprostaticaly, intrapleurally, intratracheally, intravitreally, intravaginally, intrarectally, intratumorally, intramuscularly, intraperitoneally, subcutaneously, subconjunctival, intravesicularlly, mucosally, intrapericardially, intraumbilically, intraocularally, intrathecally, locally, by injection, by infusion, by continuous infusion, by localized perfusion bathing target cells directly, via a catheter, or via a lavage. For example, the composition may be administered by injection or infusion.

To have a better therapeutic benefit, the nanoparticle or nanoparticle formulation may be administered in combination with at least an additional therapy such as radiation or light-based therapy and/or agent such as a radiotherapeutic agent, a hormonal therapy agent, an immunotherapeutic agent, a chemotherapeutic agent, a cryotherapeutic agent and/or a gene therapy agent.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions of the invention can be used to achieve methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 6A-B: In vivo comparison of signal to noise ratios (SNR) (FIG. 6A) and contrast to noise ratios (CNR) (FIG. 6B) for different liposomal-Gd agents. Each agent was administered in mice at a lipid dose of 200 mg/kg. There was significant difference within the SNRs and CNRs of various contrast agents ($p<0.05$).

FIG. 7: Larger liposomes/miscelles are retained in tumors; whereas, smaller ones enter tumors earlier and then leave within 48 hours. Rhodamine labeled liposomes/miscelles were injected into nude mice bearing subcutaneous tumors.

FIGS. 8A-D: Targeted liposomes bind to cells expressing SSTR2. At 37° C., uptake of liposomes displaying octreotide and containing carboxyfluorescein is seen by cells expressing SSTR2 (FIG. 8A) and competed by free octreotide (FIG. 8B). Binding is not seen with untargeted liposome (FIG. 8C), but is seen with targeted liposome upon exposure for one hour at 4° C. to test for binding without internalization (FIG. 8D).

FIG. 9: Effect of Gd concentration on T1 relaxation is bimodal. The bladder of a patient with no contrast anteriorly (anterior) and increasing concentration of gadolinium-based contrast agent posteriorly (posterior). Note increase and then decrease in signal with increasing gadolinium concentration. The Gd-based contrast agent is more dense than urine and settles to the bottom.

DESCRIPTION OF ILLUSTRATIVE EMBODIMENTS

Figure 1:
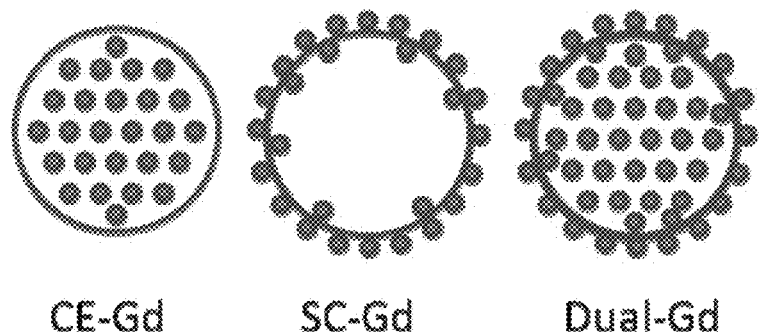
FIG. 1: Schematic of various liposomal-Gd agents. Core-encapsulated gadolinium (CE-Gd) liposomes contain conventional low molecular-weight Gd-chelates in the core interior of the liposomes, surface-conjugate gadolinium (SC-Gd) liposomes contain Gd-chelates conjugated on the internal and external surface of the liposome bilayer, Dual-Gd liposomes contain both core-encapsulated and surface-conjugated Gd-chelates. The small blue circles represent Gd-chelates.

The present invention is based, in part, on the discovery that nanoparticle-based gadolinium (Gd) agents which contain both core-encapsulated Gd as well as surface-conjugated Gd ("dual-Gd" agents) can exhibit significant advantages for imaging, e.g., using T1-weighted MRI. The imaging agents of the present invention provide, in various embodiments, improvements over previous imaging agents having either core-encapsulated Gd (CE-Gd) liposomes or surface-conjugated Gd (SC-Gd) liposomes. The development of such imaging agents may be particularly useful in the field of molecular MRI where the targets of interest, such as tumor cells or cell-associated molecules, are present at micro- or nano-molar concentrations. As shown in the below examples, liposomes containing core-encapsulated and surface-conjugated gadolinium can result in increased delivery of Gd, improved signal enhancement per particle signal to noise ratios (SNR), improved contrast to noise ratios (CNR), and/or improved nanoparticle-based T1 relaxivity.

The need to increase MRI image contrast, both as measured by signal-to-noise (overall brightness) and contrast-to-noise (feature conspicuity) is a constant thrust in the field of contrast agent development. Nanoparticle-based contrast agents may be used to amplify signal by delivering more contrast agent molecules to an area of interest; therefore, improving both overall signal and feature conspicuity. For vascular imaging, SNR and CNR may be improved by nanoparticle contrast agents with (1) decreased propensity for indiscriminate extravasation, thus, reducing vessel blurring; and, (2) long intravascular circulation time, thus, reducing the need for bolus tracking. This may permit acquisition of high-resolution scans with several image signal averages. Nanoparticles of the present invention may be used in certain embodiments for small feature analysis, e.g., that is critical in imaging of small animals and in clinical decision making In addition, the capability to deliver increased payload of Gd may be attractive for molecular imaging. Molecular targeting of individual contrast molecules typically results in a 1:1 target-to-readout ratio. Since molecular targets, such as receptors present in the vasculature, are often present in micro- or nano-molar concentrations, readouts may also typically be in this concentration range. This has made molecular imaging the domain primarily of nuclear imaging methods, which have high sensitivity to detect such low concentration ranges. With nanoparticles such as dual Gd, the ratio of contrast agent to target can be dramatically increased so that thousands of imaging agents are localized per particle bound to the target. Thus, measuring the relaxivity on a particle-molar basis is a good way of estimating the signal achievable for nanoparticle-based contrast agents (Winter et al., 2003).

Nanoparticles

In certain aspects, the present invention affords compositions and methods involving a nanoparticle formulation comprising a nanoparticle having both core-encapsulated and surface conjugated imaging agent, such as a gadolinium-containing contrast agent.

As used herein, the term "nanoparticle" refers to any particles having dimensions in the 1-1000 nm range. The term nanoparticle may be used to describe objects of from 1 to 300 nm in diameter represented by vesicles, polymers or colloids. These species are used for drug delivery and for diagnostic purposes. The nanoparticle may have a particle diameter of less than 1000 nm, about 1 nm to about 500 nm, about 10 to 200 nm, about 20 to about 200 nm, about 20 to about 100 nm, about 20 to about 30 nm, or any range derivable therein. The particle diameter may be a mean or an average diameter. The term nanoparticles in certain aspects of the present embodiments includes particles that have a diameter of about 1, 2, 3, 4, 5, 6, 7, 8, 9, 10, 11, 12, 13, 14, 15, 16, 17, 18, 19, 20, 25, 30, 31, 32, 33, 34, 35, 40, 45, 50, 55, 60, 65, 70, 75, 80, 85, 90, 95, 100, 150 or 200 nm, or any intermediate ranges. In certain aspects, the nanoparticles may be conjugated to a targeting moiety to provide structures with potential application for targeted delivery, controlled release, enhanced cellular uptake and intracellular trafficking in vitro and in vivo.

A variety of gadolinium-containing contrast agents or gadolinium chelates may be included on the surface and/or in the interior of a liposome or dual-Gd liposome in various embodiments of the present invention. For example, the liposome may comprise one or more of: gadodiamide (e.g., Omniscan), gadobenic acid or gadobenate dimeglumine (e.g., Multihance), gadopentetic acid or gadopentetate dimeglumine (e.g., Magnevist), gadoteridol (e.g., Prohance), gadofosveset (e.g., Vasovist, Ablavar), gadoversetamide (e.g., OptiMARK), gadoxetic acid (e.g., Eovist in the USA, Primovist in other parts of the world), gadobutrol (e.g., Gadavist in the USA, Gadovist in Canada and Europe), gadoteric acid (e.g., Dotarem), gadoxetic acid disodium (e.g., Primovist), gadobutrol, gadocoletic acid, gadodenterate, gadomelitol, and/or gadopenamide. The gadolinium-containing contrast agents or gadolinium chelates may be core-encapsulated and/or surface-conjugated in a Dual-Gd liposome or nanoparticle of the present invention. In certain preferred embodiments, a first gadolinium chelate compound is comprised in the liposome as a surface-conjugated imaging agent, and a second gadolinium chelate compound is comprised in the liposome as a core-encapsulated imaging agent.

In some embodiments, the following method may be used to generate nanoparticle-based gadolinium (Gd) agents that contain both core-encapsulated Gd as well as surface-conjugated Gd. Two different gadolinium chelates may be included in the nanoparticles to generate nanoparticles containing a substantially surface-conjugated gadolinium chelate (e.g., Gd-DTPA-BSA) and a substantially core encapsulated gadolinium (e.g., gadobenate dimeglumine). A lipid mixture consisting of DPPC, Gd-DTPA-BSA, Cholesterol and mPEG2000-DSPE in the molar ratio of about 30:25:40:5 may be dissolved in a chloroform:methanol (about 1:1 v/v) mixture. In various embodiments of the present invention, the molar ratios of DPPC, Gd-DTPA-BSA, Cholesterol and mPEG2000-DSPE may be varied. The solvent mixture may then be evaporated to dryness under vacuum and the lipid contents hydrated with a solution of gadobenate dimeglumine (Multihance®, Gd-BOPTA, 500 mM Gd) to achieve a lipid concentration of about 40 mM. In this way, the resulting liposomes may contain one chelated gadolinium compound (i.e., Gd-DTPA-BSA) conjugated to, substantially contained within, or associated with the surface of the liposome, and the other chelated gadolinium compound (i.e., gadobenate dimeglumine) substantially core-encapsulated or contained within the interior of the liposome. The solution may then be stirred for about 90 minutes at about 60° C. and then sequentially extruded five passes through 400 nm Nuclepore membrane, seven passes through 200 nm Nuclepore membrane and ten passes through 100 nm Nuclepore membrane. A variety of filters (e.g., having pre sizes of about 50-500 nm or 100-400 nm) may be used to substantially purify or isolate nanoparticles of a certain size range. The resulting solution may be diafiltered using a MicroKros® module (Spectrum Laboratories, CA) of 500 kDa molecular weight cut-off to substantially remove unencapsulated Gd-chelate molecules.

The liposome may comprise, include, or be coupled to a targeting moiety to increase accumulation or binding of the liposome to a particular cell or tissue type (e.g., a cancerous tissue or a tumor). For example, the liposome can be conjugated to a variety of targeting moieties, such as small molecules, peptides, antibodies (including monoclonal and recombinant antibodies and antibody fragments), nucleic acids, and/or aptamers. Targeting moieties can be attached or coupled covalently or non-covalently, and can be attached or coupled via a conjugation linker Some linkers include polyethylene glycol (PEG) chains. In certain aspects, PEG chains may be terminated at one end by a hydrazide moiety and/or at the other end by two thiol groups. In the case of antibodies and other amino acid containing moieties, the protein can be exposed to $NaIO_4$, thereby oxidizing the hydroxyl moieties on the polypeptide to aldehyde groups. The formation of the aldehyde groups can be colorimetrically confirmed using a standard assay with an alkaline Purpald solution (Sigma). Excess linker can be added to the oxidized polypeptide. The linker interacts with aldehyde groups on the polypeptide to form a stable linkage. Unreacted linker can then be removed by filtration. After purification, the modified polypeptides can be mixed with gold nanoparticles in a buffer. During this step a stable bond is formed between the surface and a linker thiol group. Monofunctional PEG-thiol molecules can be added to passivate the remaining nanoparticle surface. The conjugates can be centrifuged and resuspended in an appropriate buffer.

In certain aspects, the nanoparticle may further comprise a surface stabilizer and/or targeting agent. Non-limiting examples of surface stabilizer include citrate, polyacetylene glycol, cysteine, folic acid, polypropylene glycol, copolymers of polyethylene glycol and polypropylene glycol, polylysine, polyvinyl alcohol, human serum albumin, bovine serum albumin, hyaluronic acid, polyethyleimine (PEI), polyvinylprrolidone (PVP) or any chemical compound that passivates the surface of nanoparticle and protects the nanoparticle from further growth. For example, the polyacetylene glycol is polyethylene glycol (PEG). The polyethylene glycol may have a molecular weight ranging from 100-20,000 dalton, or more particularly, from 1000-5000 dalton. For example, the PEG may have at least, at most or about 100, 200, 300, 400, 500, 600, 700, 800, 900, 1000, 2000, 3000, 4000, 5000, 6000, 7000, 8000, 9000, 10,000, 20,000, 30,000, 40,000, 50,000 dalton, or any range derivable therefrom. In some aspects, the surface stabilizer can also act as a targeting agent (e.g., hyaluronic acid and folic acid can be used to target particular classes of tumor cells).

The surface stabilizer may be virtually composed of a monomolecular layer. The surface property of nanoparticles, particularly property of the surface stabilizer layer, could determine the solubility, chemical reactivity, biodistribution, or pharmacokinetic properties of nanoparticles. Very small size, uniformity of particles, and critical role of the surface distinguishes nanoparticles from both colloidal and molecular systems.

Dual-Gd liposomes may include a stabilizer such as PEG. Dual-Gd liposomes may include or utilize a PEGylated (Stealth) liposome platform. The PEGylated liposome platform may, in certain embodiments, have several advantages. Firstly, it is a versatile platform, as demonstrated by the easy preparation of 3 different variants in the below examples (CE, SC and Dual). Second, there is much known about the safety and disposition of such liposomes in the body; indeed, there are therapeutic products already in clinical use that are based on this platform. The safety and disposition of Gd-based liposomal agents may be further investigated. The long circulating property of Stealth liposomes, coupled with their extravasation in regions of altered vasculature or vascular compromise, make this class of agents quite attractive for visualizing vascular lesions. Moreover, there is much known about the molecular targeting of Stealth liposomes (Ghaghada et al., 2005; Saul et al., 2003; McNeeley et al., 2009). To capitalize on these advantages, improving the T1 relaxivity per particle is critical. The orders of magnitude improvement in relaxivity achieved per nanoparticle with Dual-Gd compared to conventional Gd-chelate agents may enable improved vascular imaging and/or allow for molecularly-targeted MR imaging.

In some embodiments the nanoparticles of the present invention comprise PEGylated or stealth liposomes. Stealth liposomes typically include some form of the synthetic polymer poly-(ethylene glycol) (PEG) in liposome composition. The presence of PEG on the surface of the liposomal carrier has been shown to extend blood-circulation time while reducing mononuclear phagocyte system uptake. In some embodiments synthetic modification of the terminal PEG molecules may be performed to couple the liposomes to a targeting moiety, such as, e.g., a monoclonal antibody or ligand. Stealth liposomes are well known in the art (see, e.g., Immordino et al., 2006).

In certain aspects the nanoparticles, such as liposomes or micelles, may contain an imaging agent both on the surface and inside the nanoparticle. The imaging agent may be a MR contrast agent such as, for example, a T1- or T2-shortening agent, Gd, a lanthanide, manganese, iron, a paramagnetic, superparmagnetic, or hyperpolarized agent. The nanoparticles may contain an additional imaging agent, such as, e.g., iodine, a radioactive substance for gamma-camera or PET imaging (e.g., 99m-Tc, 131-I, 67-Ga, 68-Ga, 18-F, etc.), or an optical imaging agent for detecting the nanoparticle with visible light, near-infrared (NIR), and infrared (IR) light (e.g., FITC, rhodamine and Cy5.5 and mixtures thereof). The examples agents given are a short list and not inclusive of the many imaging agents, for example, Alexa dyes are not mentioned, but may be used. The same agent may be both encapsulated and on the surface. In particular embodiments, two or more agents may be surface-conjugated and/or core-encapsulated in the liposome. "Surface-conjugated", as used herein, refers to at least a portion of a compound being substantially within the encapsulating material, such as lipid bilayer, or chelated or covalently bound to a compound that is substantially within the encapsulating material. The nanoparticle may comprise a therapeutic agent, such as a core-encapsulated and/or surface-conjugated therapeutic agent. The nanopartilce may be used in vitro and/or in vivo. An example nanoparticle such as a liposome may be modified to be a stealth liposome. The nanoparticle may be a liposome that has been modified to be cleavable. In some embodiments, the nanoparticle may be a targeted liposome. In particular embodiments, the imaging agent is a chelated gadolinium molecule. The liposome or micelle may be modified to be stealth liposome or stealth micelle. In particular embodiments, the liposome or micelle is modified to be a cleavable liposome, including cleavable stealth liposome or micelle. In particular embodiments, the liposome or micelles specifically are targeted to a particular cellular target, e.g., a G-protein such as the somatostatin receptor family (e.g., somatostatin receptor type 2). Depending on the imaging agent incorporated, in vitro uses may include a variety of imaging methodologies, including but not limited to light based imaging techniques such as microscopy, or higher resolution techniques such as electron microscopy. In vitro therapeutic techniques may include but are not limited to drug screening, tissue diagnosis, and FACS analysis. In vivo, the invention may be visible by multiple imaging modalities, including but not limited to computed tomography, magnetic resonance imaging, light based imaging, ultrasound and nuclear medicine based techniques. This may be used for diagnosing, staging, or monitoring biology or disease as well as predict response to a therapy; and, may carry a therapeutic drug, for example, a tumorostatic or tumoricidal agent. In some embodiments, both an imaging and a therapeutic agent may be substantially simultaneously delivered to a subject in a single liposome formulation, for example, to simultaneous visualize and treat the lesion.

The nanoparticles or liposomes of the present invention may be used for a variety of clinical applications. For example, the nanoparticles may be used for in vivo vascular imaging, e.g., for assessing the competence of the vasculature and assessing the degree of stenosis, for example, for assessing renal artery stenosis, carotid artery stenosis, coronary artery stenosis, stenoses of other arteries including in the thorax, abdomen, limbs and head; thus, may be of use in multiple fields including cardiology, interventional radiology, vascular surgery, etc. Untargeted nanoparticles often accumulate in areas of atherosclerosis, thus nanoparticles of the present invention may be used in certain embodiments for plaque imaging which is an important goal in cardiology. Untargeted nanoparticles may also be used for imaging lymph nodes, such as sentinel lymph nodes, and/or to outline or identify one or more tumor in a lymph node. Untargeted nanoparticles may accumulate in tumors and be used for predicting/assessing response. Targeted nanoparticles may be used for detection, prognostication, predicting, and/or assessing response of a disease, such as atherosclerosis or cancer. The nanoparticles may also be used in certain embodiments for neuroimaging, such as imaging a patient who has or is suspected of having Alzheimer's disease.

In some embodiments, dual-Gd nanoparticles of the present invention may be used to visualize vasculature such as, e.g., areas of low vascular leak that surround a tumor. Several nanoparticle-based platforms have been utilized to develop signal amplification contrast agents (Tran et al., 2007; Frias et al., 2004; Kobayashi and Brechbiel, 2005). Liposomes have been used for preparation of two separate Gd-based constructs: core-encapsulated Gd (CE-Gd) liposomes wherein the Gd-chelates are encapsulated in the interior core of liposomes (Tilcock et al., 1989; Ghaghada et al., 2008); and surface-conjugated Gd (SC-Gd) liposomes wherein the Gd-chelates are presented on the surface of liposomes (Mulder et al., 2004). Compared to conventional Gd-chelates, liposomal-Gd agents can display a longer in vivo half life and may have very low propensity to extravasate except at regions of 'leaky' vasculature, such as tumor blood vessels (Ishida et al., 1999; Gabizon et al., 2003; Ayyagari et al., 2006). As a result, these agents provide an extended imaging window for acquisition of high-resolution images, thus enabling improved small vessel depiction. This has been demonstrated previously by imaging of sub-millimeter vascular features of the CNS neurovasculature (Ghaghada et al., 2007) and the cardiovascular system (Bucholz et al., 2008) in small animals. From a molecular MRI perspective, such nanoparticle agents are able to deliver a high payload of Gd-chelates to the target site and therefore amplify signal. In addition to molecular targeting, such nanoparticle agents may be used for highlighting or identifying areas with low levels of vascular leak as observed in tumors (Karathanasis et al., 2009).

As shown in the below examples, dual-Gd nanoparticles can, in various embodiments, exhibit advantages over previously used MRI imaging agents. Several macromolecular and nanoparticle-based platforms have been investigated for the development of blood pool and molecular MRI contrast agents. MS-325, an albumin-binding Gd-chelate was recently approved for use as a blood pool MR contrast agent in USA. While the agent is known to demonstrate persistent blood pool contrast, the mechanism of action is based on transient interactions with human serum albumin (HSA) and therefore is likely to exhibit variability in signal enhancement due to on-off binding (Port et al., 2005). In the nanoparticle-domain, three major platforms have been investigated. Lipid-based paramagnetic perfluorocarbon (PFC) nanoparticles have been used as molecular MRI contrast agents for several targets (Tran et al., 2007). The mean diameter of PFC-nanoparticles is around 250 nm, thus enabling higher surface incorporation of Gd per nanoparticle and therefore higher nanoparticle-based relaxivity compared to Dual-Gd agents. Dendrimers-based gadolinium nanoparticles have also been extensively investigated for use as blood pool and molecular MRI contrast agents (Kobayashi and Brechbiel, 2005). The use of dendrimer as a platform enables synthesis of a broad range of particle sizes. Additionally, the payload of Gd that can be delivered is limited by the number of conjugation sites available on the dendrimer. Liposomes have also been extensively investigated for use as contrast agents. However, a particular problem with CE-Gd liposomes has been the inability to generate a large amount of T1 relaxivity due to limited proton exchange between the interior and exterior of liposomes because of the liposomal bilayer (Ghaghada et al., 2008). The presentation of Gd-chelates on the surface of nanoparticles in SC-Gd liposomes have resulted in equal or higher T1 relaxivities compared to conventional contrast agents. However, the number of sites for Gd chelate conjugation on the liposome are limited to about 25% of the number of surface lipid molecules because larger percentages tend to destabilize the membrane (Mulder et al., 2004). Although this limits the total enhancement that is achievable using surface Gd, alternate liposome-based structures that exhibit higher relaxivity are feasible and could further improve image quality. Liposomes containing Gd-chelates complexed to very short polymeric chains of ethylene glycol (PEG) have also been investigated (Storrs et al., 1995). The complexation of Gd on the flexible polymers resulted in higher T1 relaxivity on a Gd-basis. The relatively short PEG chains (2 monomer units) can result in faster clearance.

As observed in the below examples, dual-Gd nanoparticles displayed improved relaxivity. The T1 relaxivities of free Gd chelates are on the order of 3-5 $(mM \cdot sec)^{-1}$; whereas, Dual-Gd were observed in the below examples to provide a nanoparticle-based T1 relaxivity of about 35000 $(mM \cdot sec)^{-1}$, which is approximately $10^4$ times higher than that of free Gd chelate. The development of such nanoparticles with high signal amplification begins to bring molecular imaging into the realm of MRI. This in turn has huge potential advantages since MRI, unlike nuclear imaging techniques, can demonstrate anatomy along with the molecular target, with enormously high spatial resolution and without exposure of the subject to radioactivity.

Improved relaxivity of the nanoparticles of the present invention may result in reduced toxicity. Another key parameter that characterizes a nanoparticle-based contrast agent is the number of particles injected in order to generate sufficient image contrast. This has implications ranging from the potential for infusion-related reactions to the ultimate clearance route and toxicity. Infusion related reactions, which can cause complement-activation related pseudoallergies (CARPA), are sensitive to physicochemical properties of nanoparticles (Szebeni, 2005). Clearance of nanoparticles is usually via the reticulo-endothelial system (RES), and a high particle load could lead to RES overload, thus compromising the body's ability to clear other particulate species. A lower dose of a contrast agent with high relaxivity can be injected to achieve the same signal enhancement as a larger quantity of an agent with lower relaxivity. Thus, the relaxivity on a molar basis of nanoparticles is critically important to avoid toxicity and other complications.

Nanoparticle Therapeutic Agents

The nanoparticles of the present invention may optionally include one or more additional therapeutic agents. In some embodiments, the therapeutic agent may be comprised (e.g., surface-conjugated or core-encapsulated) in a liposome, such as a dual-Gd liposome. The therapeutic agent may be a chemotherapeutic agent. In some embodiments, a nanoparticle of the present invention may be used to both image a tissue (e.g., a tumor) and deliver a therapeutic to that tissue (e.g., deliver a chemotherapeutic to the tumor).

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromefihylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein tansferase inhibitors, transplatinum, 5-fluorouracil, vincristine, vinblastine and methotrexate and pharmaceutically acceptable salts, acids or derivatives of any of the above.

Also included in the compositions may be antibiotic agents and/or anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene; aromatase inhibitors that inhibit the enzyme aromatase, which regulates estrogen production in the adrenal glands, such as, for example, 4(5)-imidazoles, aminoglutethimide, megestrol acetate, exemestane, formestanie, fadrozole, vorozole, letrozole, and anastrozole; and anti-androgens such as flutamide, nilutamide, bicalutamide, leuprolide, and goserelin; as well as troxacitabine (a 1,3-dioxolane nucleoside cytosine analog) or antitestosterone agents; antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor and a HER2 expression inhibitor; vaccines such as gene therapy vaccines and pharmaceutically acceptable salts, acids or derivatives of any of the above.

Targeting of Nanoparticles

Targeted delivery is achieved by the addition of ligands without compromising the ability of nanoparticles to deliver their loads. It is contemplated that this may enable delivery to specific cells, tissues and organs. The targeting specificity of the ligand-based delivery systems is based on the distribution of the ligand receptors on different cell types. It is preferable that the ligand to be conjugated to the nanoparticles may bind to the receptors that specifically or predominantly express in tumor cells so that the nanoparticle may be preferentially delivered to the tumor cells. For example, specific antibodies such as anti-CD20 (Rituximab) may be conjugated to the nanoparticles to deliver nanoparticles to malignant B-cells such as those of chronic lymphocytic leukemia and B-cell lymphoma.

The targeting ligand may either be non-covalently or covalently associated with a nanoparticle, and can be conjugated to the nanoparticles by a variety of methods as discussed herein. Examples of proteins or peptides that can be used to target nanoparticles include transferin, lactoferrin, TGF-α, nerve growth factor, albumin, HIV Tat peptide, RGD peptide, and insulin, as well as others (Gupta et al., 2005; Ferrari, 2005).

In further aspects, the nanoparticle may be coupled to a tumor targeting moeity. In certain embodiments the tumor targeting moiety is an antibody that binds an antigen selected from the group consisting of, a gastrointestinal cancer cell surface antigen, a lung cancer cell surface antigen, a brain tumor cell surface antigen, a glioma cell surface antigen, a breast cancer cell surface antigen, an esophageal cancer cell surface antigen, a common epithelial cancer cell surface antigen, a common sarcoma cell surface antigen, an osteosarcoma cell surface antigen, a fibrosarcoma cell surface antigen, a melanoma cell surface antigen, a gastric cancer cell surface antigen, a pancreatic cancer cell surface antigen, a colorectal cancer cell surface antigen, a urinary bladder cancer cell surface antigen, a prostatic cancer cell surface antigen, a renal cancer cell surface antigen, an ovarian cancer cell surface antigen, a testicular cancer cell surface antigen, an endometrial cancer cell surface antigen, a cervical cancer cell surface antigen, a Hodgkin's disease cell surface antigen, a lymphoma cell surface antigen, a leukemic cell surface antigen and a trophoblastic tumor cell surface antigen.

In particular embodiments, the tumor targeting moiety is an antibody, antibody fragment, or ligand that binds an antigen or a receptor selected from the group consisting of 5 alpha reductase, α-fetoprotein, AM-1, APC, APRIL, BAGE, β-catenin, Bc12, bcr-abl (b3a2), CA-125, CASP-8/FLICE, Cathepsins, CD19, CD20, CD21, CD23, CD22, CD38, CD33, CD35, CD44, CD45, CD46, CD5, CD52, CD55, CD59 (791Tgp72), CDC27, CDK4, CEA, c-myc, Cox-2, DCC, DcR3, E6/E7, EGFR, EMBP, Ena78, FGF8b and FGF8a, FLK-1/KDR, Folic Acid Receptor, G250, GAGE-Family, gastrin 17, GD2/GD3/GM2, GnRH, GnTV, gp100/Pme117, gp-100-in4, gp15, 75/TRP-1, hCG, Heparanase, Her2/neu, HERS, Her4, HMTV, HLA-DR10, Hsp70, hTERT, IGFR1, IL-13R, iNOS, Ki 67, KIAA0205, K-ras, H-ras, N-ras, KSA, (CO17-1A), LDLR-FUT, MAGE Family (MAGE1, MAGE3, etc.), Mammaglobin, MAP17, Melan-A/, MART-1, mesothelin, MIC A/B, MT-MMP's, such as MMP2, MMP3, MMPI, MMP9, Mox1, MUC-1, MUC-2, MUC-3, and MUC-4, MUM-1, NY-ESO-1, Osteonectin, p15, P170/MDR1, p53, p97/melanotransferrin, PAI-1, PDGF, Plasminogen (uPA), PRAME, Probasin, Progenipoietin, PSA, PSM, PSMA, RAGE-1, Rb, RCAS1, SART-1, SSX gene, family, STAT3, STn, TAG-72, TGF-α, TGF-β, and Thymosin β15, nucleolin, Ca15-3, astro Intestinal Tumor Antigen (Ca19-9), ovarian Tumor Antigen (Ca125), Tag72-4 Antigen (CA72-4) and carcinoembryonic antigen (CEA). In a particular example, the targeting ligand may be a CD44 binding ligand, such as hyaluronic acid (HA).

Nanoparticles for Imaging

In certain preferred embodiments, nanoparticles of the present invention are use for Magnetic resonance imaging (MRI). MRI is an imaging modality that uses a high-strength magnet and radio-frequency signals to produce images. The most abundant molecular species in biological tissues is water. It is the quantum mechanical "spin" of the water proton nuclei that ultimately gives rise to the signal in imaging experiments and other nuclei can also be imaged. In MRI, the sample to be imaged is placed in a strong static magnetic field (1-12 Tesla) and the spins are excited with a pulse of radio frequency (RF) radiation to produce a net magnetization in the sample. Various magnetic field gradients and other RF pulses then act on the spins to code spatial information into the recorded signals. By collecting and analyzing these signals, it is possible to compute a three-dimensional image which, like a CT, SPECT, and PET image, is normally displayed in two-dimensional slices. The slices may be combined to build three-dimensional representations. Contrast agents used in MR or MR spectroscopy imaging differ from those used in other imaging techniques. Their purpose is to aid in distinguishing between tissue components with similar signal characteristics and to shorten the relaxation times (which will produce a stronger signal on T1-weighted spin-echo MR images and a less intense signal on T2-weighted images). Examples of MRI contrast agents include gadolinium chelates, manganese chelates, chromium chelates, and iron particles such as iron oxide particles or iron platinum particles.

MRI may be used for a variety of purposes. For example, high resolution images may provide information regarding a cancer or tumor extent, while functional magnetic resonance imaging techniques can be used to quantify tissue characteristics, or in surgical planning, to identify nearby critical structures, that should be avoided during a surgical treatment. MRI may be applied in a post-treatment setting in order to gauge success or monitor for recurrence. MRI may also be used to measure anatomic, functional, or macroscopic characteristics of tumor tissue to test for early indications of response to therapy. MRI may also be used as a screening tool, e.g., in high-risk populations.

High field experimental MRI performed at 4.7 T and above may be used to visualize tissues, e.g., in pre-clinical oncology. Compared to common clinical field strengths (1.5 T), high field scanners provide more than three times the spectral resolution in spectroscopy and spectroscopic imaging applications. In addition, higher field strength offers an increased signal-to-noise ratio (SNR) that can allow the acquisition of higher resolution images, approaching the same anatomically relative resolution in small animal models of disease as are routinely achieved in a clinical setting. Animal models provide a consistent 'patient' population on which early toxicity and dose response, or functional or molecular studies can be completed. Contrast agents and imaging probes can be utilized in human subjects or non-human animals.

Although certain embodiments of the present invention relate to using gadolinium-containing nanoparticles (e.g., dual-Gd liposomes) in MRI, a radioactive gadolinium ($^{152}$Gd) may be included in the nanoparticles, and the nanoparticles may be used in PET or SPECT. The six naturally-occurring isotopes of gadolinium are: $^{154}$Gd, $^{155}$Gd, $^{156}$Gd, $^{157}$Gd, $^{158}$Gd and $^{160}$Gd, and 1 radioisotope, $^{152}$Gd. Positron emission tomography (PET) is a powerful and widely used diagnostic tool that has the advantages of high sensitivity (down to the picomolar level) and ability to provide quantitative imaging analyses of in vivo abnormalities (Scheinin et al., 1999; Eckelman, 2003; Welch et al., 2009). In other embodiments, the nanoparticles may be used for PET, SPECT, CT, ultrasound or photoacoustic tomography.

Nanoparticles may also be used in SPECT. Single photon emission computed tomography (SPECT, or less commonly, SPET) is a nuclear medicine tomographic imaging technique using gamma rays. It is very similar to conventional nuclear medicine planar imaging using a gamma camera. However, it is able to provide true 3D information. This information is typically presented as cross-sectional slices through the patient, but can be freely reformatted or manipulated as required.

The SPECT basic technique requires injection of a gamma-emitting radioisotope called radionuclide) into the bloodstream of the patient. In certain aspects the radioisotope is integrated into a nanoparticle, which has chemical properties which allow it to be concentrated in ways of medical interest for disease detection. In other aspects, a nanoparticle comprising a marker radioisotope, which is of interest for its radioactive properties, has been attached to a targeting ligand, which is of interest for its chemical binding properties to certain types of tissues. This marriage allows the combination of ligand and radioisotope (the radiopharmaceutical) to be carried and bound to a place of interest in the body, which then (due to the gamma-emission of the isotope) allows the ligand concentration to be seen by a gamma-camera.

Nanoparticles may also be used in CT. Computed tomography (CT) is a medical imaging method employing tomography created by computer processing. Digital geometry processing is used to generate a three-dimensional image of the inside of an object from a large series of two-dimensional X-ray images taken around a single axis of rotation. CT is used in medicine as a diagnostic tool and as a guide for interventional procedures. Sometimes contrast materials such as intravenous iodinated contrast are used. This is useful to highlight structures such as blood vessels that otherwise would be difficult to delineate from their surroundings. Using contrast material can also help to obtain functional information about tissues.

Nanoparticles may also be used in photoacoustic tomography. Photoacoustic tomography (PAT), or photoacoustic computed tomography (PACT), is a materials analysis technique based on the reconstruction of an internal photoacoustic source distribution from measurements acquired by scanning ultrasound detectors over a surface that encloses the source under study. The PA source is produced inside the object by the thermal expansion that results from a small temperature rise, which is caused by the absorption of externally applied radiation of pulsed electromagnetic (EM) waves. This technique has great potential for applications in the biomedical field because of the advantages of ultrasonic resolution in combination with EM absorption contrast. PAT is also called optoacoustic tomography (OAT) or thermoacoustic tomography (TAT), with the term "thermoacoustic" emphasizing the thermal expansion mechanism in the PA generation. OAT refers particularly to light-induced PAT, while TAT is used to refer to rf-induced PAT.

In photoacoustic tomography (PAT), each temporal PA signal, measured at various detection positions, provides one-dimensional radial information about the PA source relative to the detector position; 2D surface scans offer other 2D lateral information about the PA source. Combining the temporal and spatial measurements affords sufficient information for a complete reconstruction of a 3D PA source. Because the PA signal received by each ultrasound detector is the integral of the ultrasound waves over the sensing aperture of the detector, the reconstruction algorithms depend on the detector apertures as well as the scanning geometries. Small-aperture detectors are often used to approximate point detectors, which receive PA signals originating from spherical shells, centered at each point detector, with radii determined by the acoustic times of flight. The three geometries commonly used are planar, cylindrical, and spherical surfaces. Both Fourier- and time-domain reconstruction formulas with point-detector measurements for these geometries have been well established. Besides, algorithms based on other detection methods, such as large-aperture (plane), line, or circle detectors have also been derived.

Pharmaceutical Preparations

When administering nanoparticles to a subject, such as a human patient, it will generally be beneficial to prepare the particles as a pharmaceutical composition appropriate for the intended application. This may entail preparing a pharmaceutical composition that is essentially free of pyrogens, as well as any other impurities that could be harmful to humans or animals. One may also employ appropriate buffers to render the complex stable and allow for uptake by target cells.

The phrase "pharmaceutical or pharmacologically acceptable" refers to molecular entities and compositions that do not produce an adverse, allergic or other untoward reaction when administered to an animal, such as a human, as appropriate. For animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art. A pharmaceutically acceptable carrier is preferably formulated for administration to a human, although in certain embodiments it may be desirable to use a pharmaceutically acceptable carrier that is formulated for administration to a non-human animal but which would not be acceptable (e.g., due to governmental regulations) for administration to a human. Except insofar as any conventional carrier is incompatible with the active ingredient, its use in the therapeutic or pharmaceutical compositions is contemplated.

The actual dosage amount of a composition of the present invention administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound, such as the nanoparticle or the integrated Gd. In other embodiments, the active compound may comprise between about 1% to about 75% of the weight of the unit, or between about 5% to about 50%, for example, and any range derivable therein. In other non-limiting examples, a dose may also comprise from about 1 microgram/kg/body weight, about 50 microgram/kg/body weight, about 100 microgram/kg/body weight, about 500 microgram/kg/body weight, about 1 milligram/kg/body weight, about 5 milligram/kg/body weight, about 10 milligram/kg/body weight, about 30 milligram/kg/body weight, about 40 milligram/kg/body weight, about 50 milligram/kg/body weight, about 100 milligram/kg/body weight, or more per administration, and any range derivable therein. In non-limiting examples of a derivable range from the numbers listed herein, a range of about 5 microgram/kg/body weight to about 5 milligram/kg/body weight, about 50 microgram/kg/body weight to about 50 milligram/kg/body weight, etc., can be administered.

A nanoparticle may be administered in a dose of 1, 2, 3, 4, 5, 6, 7, 8, 9, 10, 15, 20, 25, 30, 40, 50, 60, 70, 80, 90, 100 or more mg of nanoparticle per dose. Each dose may be in a volume of 1, 10, 50, 100, 200, 500, 1000 or more μl or ml.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

Nanoparticles of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Hyperproliferative Diseases

In certain embodiments of the invention, a therapeutically effective amount of the pharmaceutical composition comprising a nanoparticle formulated in a pharmaceutically acceptable nanoparticle formulation may be used to visualize a tissue associated with a disease, e.g., visualize one or more cancerous, pre-cancerous, benign tumors in a subject. In embodiments where a nanoparticle of the present invention comprises a therapeutic agent the nanoparticle may be administered to a subject to treat a disease and/or condition in a subject. For example, dual-Gd liposomes containing a core-encapsulated chemotherapeutic to treat a hyperproliferative disease, "Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutical composition (e.g., parenterally, intravenously, etc.) comprising a nanoparticle formulated in a pharmaceutically acceptable nanoparticle formulation.

A "subject" refers to either a human or non-human, such as primates, mammals, and vertebrates. In particular embodiments, the subject is a human.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve a reduction in the size of a tumor, a reduction in the invasiveness of a tumor, reduction in the growth rate of the cancer, or prevention of metastasis. Treatment of cancer may also refer to prolonging survival of a subject with cancer.

A "disease" or "health-related condition" can be any pathological condition of a body part, an organ, or a system resulting from any cause, such as infection, genetic defect, and/or environmental stress.

A "hyperproliferative disease" includes diseases and conditions that are associated with any sort of abnormal cell growth or abnormal growth regulation, specifically a cancer.

In some embodiments of the invention, the methods include identifying a patient in need of treatment. A patient may be identified, for example, based on taking a patient history, based on findings on clinical examination, based on health screenings, or by self-referral.

Diseases

The present invention can find application in the diagnosis, management, prediction of response and treatment of any disease for which delivery of a imaging and/or therapeutic nanoparticle to a cell or tissue of a subject is believed to be of benefit. Examples of such diseases include hyperproliferative diseases and quiescent malignant diseases. In particular embodiments, the disease is a hyperproliferative disease, such as cancer of solid tissues or blood cells. Quiescent malignant diseases that can be treated by the nanoparticles include, for example, chronic lymphocytic leukemia.

For example, a nanoparticle formulated in a pharmaceutically acceptable nanoparticle formulation may be administered to visualize or treat a hyperproliferative disease. The hyperproliferative disease may be cancer, leiomyomas, adenomas, lipomas, hemangiomas, fibromas, pre-neoplastic lesions (such as adenomatous hyperplasia and prostatic intraepithelial neoplasia), carcinoma in situ, or oral hairy leukoplakia.

The cancer may be a solid tumor, metastatic cancer, or non-metastatic cancer. In certain embodiments, the cancer may originate in the bladder, blood, bone, bone marrow, brain, breast, colon, esophagus, duodenum, small intestine, large intestine, colon, rectum, anus, gum, head, kidney, liver, lung, nasopharynx, neck, ovary, prostate, skin, stomach, testis, tongue, or uterus. In certain embodiments, the cancer is ovarian cancer. In particular aspects, the cancer may be a chemo-resistant cancer.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma;

inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

Combination Treatments

In certain embodiments, the compositions and methods of the present invention involve administering to a subject a nanoparticle formulation and a second or additional therapy. Such therapy can be applied in the treatment of any disease for which treatment with the nanoparticle formulation is contemplated. For example, the disease may be a hyperproliferative disease, such as cancer. In various embodiments, a nanoparticle of the present invention may be administered to a subject in combination with a second therapeutic agent (e.g., a chemotherapy, a radiotherapy, a gene therapy, a siNA such as a siRNA or a miRNA, or an immunotherapy, etc.) or a surgery.

Combination therapies may, in certain embodiments, enhance the therapeutic or protective effect, and/or increase the therapeutic effect of another anti-cancer or anti-hyperproliferative therapy. In other embodiments, a nanoparticle (e.g., a dual-Gd liposome that does not contain a therapeutic agent) may be administered to a subject prior, during, or after administration of a therapeutic agent, such as an anti-cancer agent, to diagnose a disease or condition or to determine the effectiveness of a therapeutic given to the subject. Therapeutic and prophylactic methods and compositions can be provided in a combined amount effective to achieve the desired effect, such as the killing of a cancer cell and/or the inhibition of cellular hyperproliferation.

A nanoparticle formulation-containing composition set forth herein may be administered before, during, after or in various combinations relative to an anti-cancer treatment. The administrations may be in intervals ranging from concurrently to minutes to days to weeks. In embodiments where the nanoparticle formulation-containing composition is provided to a patient separately from an additional anti-cancer agent, one would generally ensure that a significant period of time did not expire between the time of each delivery, such that the two agents would still be able to exert an advantageously combined effect on the patient. In such instances, it is contemplated that one may provide a patient with the inhibitor of gene expression therapy and the anti-cancer therapy within about 12 to 24 or 72 h of each other and, more preferably, within about 6-12 h of each other. In some situations it may be desirable to extend the time period for treatment significantly where several days (2, 3, 4, 5, 6 or 7) to several weeks (1, 2, 3, 4, 5, 6, 7 or 8) lapse between respective administrations.

Within a single day (24-hour period), the patient may be given one or multiple administrations of the agent(s). Moreover, after a course of treatment, it is contemplated that there is a period of time at which no anti-cancer treatment is administered. This time period may last 1, 2, 3, 4, 5, 6, 7 days, and/or 1, 2, 3, 4, 5 weeks, and/or 1, 2, 3, 4, 5, 6, 7, 8, 9, 10, 11, 12 months or more, depending on the condition of the patient, such as their prognosis, strength, health, etc.

Various combinations may be employed. For the example below a therapeutic nanoparticle formulation-containing composition is "A" and an anti-cancer therapy is "B":

| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of any compound or therapy of the present invention to a patient may follow general protocols for the administration of such compounds, taking into account the toxicity, if any, of the agents. Therefore, in some embodiments there is a step of monitoring toxicity that is attributable to combination therapy. It is expected that the treatment cycles would be repeated as necessary. It also is contemplated that various standard therapies, as well as radiation and surgical intervention, may be applied in combination with the described therapy.

In specific aspects, it is contemplated that a standard therapy may include chemotherapy, radiotherapy, immunotherapy, surgical therapy or gene therapy and may be employed in combination with the inhibitor of gene expression therapy, anticancer therapy, or both the therapeutic nucleic acid and the anti-cancer therapy, as described herein.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Preparation of Liposomal Contrast Agents

For preparation of CE-Gd liposomes, a lipid mixture consisting of 1,2-Dipalmitoyl-sn-glycero-3-phosphocholine (DPPC) (Genzyme, MA), Cholesterol (Sigma-Aldrich, St Louis, MO) and 1,2-distearoyl-sn-glycero-3-phosphoethanolamine-N-[methoxy(poly(ethylene glycol))-2000] (mPEG2000-DSPE) (Genzyme, MA) in the molar ratio 55:40:5 was dissolved in ethanol. Subsequently, the ethanol solution was mixed with a solution of gadobenate dimeglumine (Multihance®, Gd-BOPTA, 500 mM Gd) to achieve a lipid concentration of 150 mM. The solution was stirred for 90 minutes at 60° C. and then sequentially extruded on a Lipex Thermoline extruder (Northern Lipids, Vancouver, British Columbia, Canada) with three passes through a 400 nm Nuclepore membrane (Waterman, Newton, MA), five passes through a 200 nm and ten passes through 100 nm membrane. The resulting solution was diafiltered using a MicroKros® module (Spectrum Laboratories, CA) of 500 kDa molecular weight cut-off to remove unencapsulated Gd-chelate molecules.

For SC-Gd liposomes preparation, a lipid mixture consisting of DPPC, Gd-DTPA bis(stearylamide) (Gd-DTPA-BSA) (IQsynthesis, St Louis, MO), Cholesterol and mPEG2000-DSPE in the molar ratio 30:25:40:5 was dissolved in a chloroform:methanol (1:1 v/v) mixture. The solvent mixture was evaporated to dryness under vacuum and the lipid contents were hydrated with 150 mM saline to achieve a lipid concentration of 40 mM. The solution was stirred for 90 minutes at 60° C. and then sequentially extruded with five passes through a 400 nm Nuclepore membrane, seven passes through a 200 nm Nuclepore membrane and ten passes through a 100 nm Nuclepore membrane.

For preparation of Dual-Gd liposomes, a lipid mixture consisting of DPPC, Gd-DTPA-BSA, Cholesterol and mPEG2000-DSPE in the molar ratio 30:25:40:5 was dissolved in a chloroform:methanol (1:1 v/v) mixture. The solvent mixture was evaporated to dryness under vacuum and the lipid contents were hydrated with a solution of gadobenate dimeglumine (Multihance®, Gd-BOPTA, 500 mM Gd) to achieve a lipid concentration of 40 mM. The solution was stirred for 90 minutes at 60° C. and then sequentially extruded five passes through 400 nm Nuclepore membrane, seven passes through 200 nm Nuclepore membrane and ten passes through 100 nm Nuclepore membrane. The resulting solution was diafiltered using a MicroKros® module (Spectrum Laboratories, CA) of 500 kDa molecular weight cut-off to remove unencapsulated Gd-chelate molecules. To demonstrate reproducibility in the synthesis process, two different batches of each liposomal agent were prepared and characterized as described below.

Characterization of Liposomal Agents
Particle Size and Composition

The size distribution of liposomes in the final formulation was determined by dynamic light scattering (DLS) using a ZetaPlus Analyzer (Brookhaven Instruments, Chapel House, UK) at 25° C. The gadolinium and phosphorus content of liposomal formulations were quantified using inductively coupled plasma optical emission spectroscopy (ICPOES; Model Optima 4300D, Perkin Elmer, Norwalk, CT) operating at a wavelength of 336.223 nm for gadolinium and 213.617 nm for phosphorus. The number of gadolinium atoms per liposome was calculated based on the Gd:P ratio, mean liposome diameter and the respective phospholipid molar composition for each formulation.

Measurement of Gd-Based Molar T1 Relaxivity

Samples with gadolinium concentrations ranging between 0.25 mM-2 mM (5 samples) were prepared by diluting the liposomal solutions in bovine plasma. T1 relaxation measurements were performed on a 60 MHz Minispec MQ series benchtop relaxometer (Bruker Optics) at 37° C. The longitudinal relaxation rates (R1) of the diluted samples were obtained using an inversion recovery method. A plot of R1 versus gadolinium concentration yielded a straight line with the slope defined as the T1 relaxivity (r1). To demonstrate reproducibility in T1 relaxation times, measurements were repeated after one week by preparing fresh dilutions in bovine plasma.

Measurement of T1 Relaxation Rates for Different Lipid Dose

The T1 relaxation rates (R1) of three liposomal contrast agents were also compared on a particle basis. Dilutions were done on a lipid-dose basis i.e., amount of lipid administered (mg) per body weight (kg). Diluted samples were prepared in bovine plasma to achieve lipid concentrations ranging between 40-400 mg lipid/kg of human body weight. The chosen concentration range represents contrast agent doses that are likely to enable sufficient SNR for in vivo imaging. To demonstrate stability and reproducibility in T1 relaxation times, measurements were repeated after one week by preparing fresh dilutions in bovine plasma.

Calculation of Nanoparticle-Based T1 Relaxivity

To calculate T1 relaxivity on a nanoparticle-basis, the above lipid-dose was converted into nanoparticle concentration. An average lipid molecular weight was determined using the molecular weight and mole fraction of each lipid used in liposome preparation. The nanoparticle concentration was then determined using the number of lipids per liposome and average lipid molecular weight. A plot of R1 versus liposome concentration yielded a straight line with the slope defined as the nanoparticle-based T1 relaxivity (r1).

In Vivo Imaging
Animal Preparation

Six nude mice were used for the studies. For in vivo comparison of different liposomal formulations, the agents were intravenously administered via the tail vein at a lipid dose of 200 mg/kg. The corresponding gadolinium doses were 0.07, 0.08 and 0.15 mmoles/kg for CE-Gd, SC-Gd and Dual-Gd, respectively. The same animals were used for all three agents, in a randomized order. On day 1, each mouse received a randomly selected agent (1: CE-Gd, 2: SC-Gd, 3: Dual-Gd). After imaging, the animals were returned to their cages for a minimum of 3 days. At the second imaging session, mice received the next agent in the list, i.e., mice that had received CE-Gd earlier then received SC-Gd, mice that had received SC-Gd earlier then received Dual-Gd and mice that had received Dual-Gd earlier then received CE-Gd. The animals then progressed to the next contrast agent in the third imaging session Inhalation of 2% isofluorane was used for anesthesia.

MR Imaging Protocol

All MR studies were performed on a 4.7 T scanner (Bruker BioSpec, 47/40 USR, Bruker Biospin, Billerica, MA) using a 60-mm gradient insert and a volume resonator with a 35 mm inner diameter. Animals were anesthetized and placed head first and prone on a positioning sled. Orthogonal 3-plane scout scans were initially acquired for animal positioning. Pre-contrast and post-contrast MRA images were acquired using a heavily T1-weighted 3D fast spoiled gradient echo sequence (FSPGR). Scans were acquired with the following imaging parameters: repetition time (TR)=5.0 ms; echo time (TE)=2.1 ms; flip angle (FA)=30°; field of view (FOV)=30×30×30 mm$^3$; Image matrix=128×128×128; number of signal averages=5. This resulted in an isotropic voxel size of 320 μm. The total scan time was under seven minutes. Maximum intensity projection (MIP) images were performed and analyzed.

Image Analysis

Signal to noise ratios (SNRs) and contrast-to-noise ratios (CNRs) were calculated for regions of interest in the jugular veins and muscle. The SNR was calculated as $SI_v/SD$ where, $SI_v$ is the mean signal intensity within the blood vessel and SD is the standard deviation of the signal intensity within the background (air). The CNR was defined as $(SI_v-SI_w)/SD$ where, $SI_m$ is the mean signal intensity in the muscle region. Pre-contrast SNRs were subtracted from post-contrast SNRs to minimize differences in baseline signals from animal to animal. Similarly, pre-contrast CNRs were subtracted from post-contrast CNRs. SNRs and CNRs calculations were performed for each animal and then average values were reported for the group (n=6).

Statistical Analysis

For comparing groups, two-tailed t-tests were performed using spreadsheet software (Microsoft Office Excel 2003, Microsoft, Seatle, WA). A P-value of less than 0.05 was considered statistically significant.

Octreotide labeled liposomes: The amine group on the lysine residue of octreotide was t-BOC protected by the addition of $BOC_2O$ along with an organic base to form Boc-Lys$^5$Octreotide. The carboxyl group on DSPE-PEG$_{2000}$-COOH was activated with di-cyclohexyl carbodiimide (DCC) to form a stable intermediate which when coupled to the Boc-Lys$^5$Octreotide forms DSPE-PEG$_{2000}$-D-Phe$^1$-BocLys$^5$Octreotide. The final step includes the deprotection of the Boc on the lysine residue to yield the product DSPE-PEG$_{2000}$-Octreotide. The proposed reaction scheme uses DMSO as the solvent, but can also be performed in DMF, Acetonitrile, methanol and Dichloromethane. The product was purified by flash column chromatography. The intermediate steps in the reaction scheme were monitored by TLC.

To make liposomes/micelles, the Octreotide conjugate was included in the lipid mixture and liposomes were formed.

Structure-activity relationship studies have shown that the N-terminal phenylalanine of octreotide can tolerate N-substitution with minimal effect on SSTR affinity and internalization rate. For maximum flexibility and binding efficiency of ligands bound to liposome surfaces, a flexible polymer tether must be used to anchor the ligand to the liposome surface. DSPE-PEG$_{2000}$-COOH and Octreotide are both commercially available at high purity. The conjugate DSPE-PEG$_{2000}$-Octreotide conjugate may be synthesized by the following method. Briefly the amine group on the lysine residue may be t-BOC protected by the addition of $BOC_2O$ along with an organic base to form Boc-Lys$^5$Octreotide. The carboxyl group on DSPE-PEG$_{2000}$-COOH may be activated with di-cyclohexyl carbodiimide (DCC) to form a stable intermediate which when coupled to the Boc-Lys$^5$Octreotide forms DSPE-PEG$_{2000}$-D-Phe$^1$-BocLys$^5$Octreotide. The final step includes the deprotection of the Boc on the lysine residue to yield the product DSPE-PEG$_{2000}$-Octreotide. The proposed reaction scheme uses DMSO as the solvent, but can also be performed in DMF, Acetonitrile, methanol and Dichloromethane. The product will be purified by flash column chromatography. The intermediate steps in the reaction scheme may be monitored by TLC. However, the identity and purity of the key intermediates can be verified by NMR and if necessary, by MALDI-TOF mass spectrometry. $^1$H-NMR spectra may be acquired on a AMX-II 600 MHZ spectrometer (Bruker Instruments, Inc.) instrument. The sample conjugates are dissolved in a suitable deuterated solvent (e.g., DMSO-d6, CDCl3 or CD3OD). MALDI-TOF spectra may be acquired on an Applied Biosystems Voyager System 4160 mass spectrometer utilizing a UV laser at 334 nm. The samples may be dissolved at concentrations of 0.5 mg/mL in either chloroform or saline containing trans-3-indoleacrylic acid (matrix).

Example 2

Dual Mode Gadolinium Nanoparticle Contrast Agent for Magnetic Resonance Imaging

The three liposomal-gadolinium formulations demonstrated good reproducibility in the fabrication process (Table 1). Size analysis of liposomes indicated particles of approximately 100 nm in diameter. The low polydispersity index for various formulations indicated narrow size distributions. More than 95% of liposomes in all the three formulations were below 150 nm. No significant changes in size distribution were observed over a one month period (data not shown). The Dual-Gd liposomes had the highest gadolinium to phospholipid (Gd:P) ratio. The calculated number of Gd per liposome were also highest for the Dual-Gd formulation. This was due to the presence of two gadolinium pools in Dual-Gd liposomes—the core-encapsulated pool and the surface-conjugated pool. Since the lipid composition and molarity for SC-Gd liposomes is similar to Dual-Gd liposomes, one would expect similar surface-Gd per liposome for both the agents. The higher Gd per liposome observed for Dual-Gd compared to the sum total of CE-Gd and SC-Gd liposomes is therefore most likely a result of increased encapsulated Gd fraction compared to the CE-Gd liposomes due to change in physiochemical properties by the core and surface combination.

TABLE 1

Characterization of liposomal-Gd formulations.

| Agent | | Mean Diameter (nm) | Polydispersity Index | Cumulative particle size distribution | | | Gd:P ratio | Gd per liposome |
|---|---|---|---|---|---|---|---|---|
| | | | | % <200 nm | % <150 nm | % <100 nm | | |
| CE-Gd | Batch-1 | 99 ± 2 | 0.054 | 100 | ≥97 | ≥75 | 0.398 | 34783 |
| | Batch-2 | 94 ± 2 | 0.022 | 100 | ≥99 | ≥80 | 0.375 | 29420 |
| SC-Gd | Batch-1 | 110 ± 3 | 0.012 | 100 | ≥95 | ≥60 | 0.784 | 49743 |
| | Batch-2 | 109 ± 3 | 0.035 | 100 | ≥96 | ≥60 | 0.782 | 48685 |
| Dual-Gd | Batch-1 | 114 ± 4 | 0.042 | 100 | ≥93 | ≥53 | 1.648 | 112590 |
| | Batch-2 | 107 ± 3 | 0.054 | 100 | ≥97 | ≥62 | 1.560 | 93462 |

Figure 2:
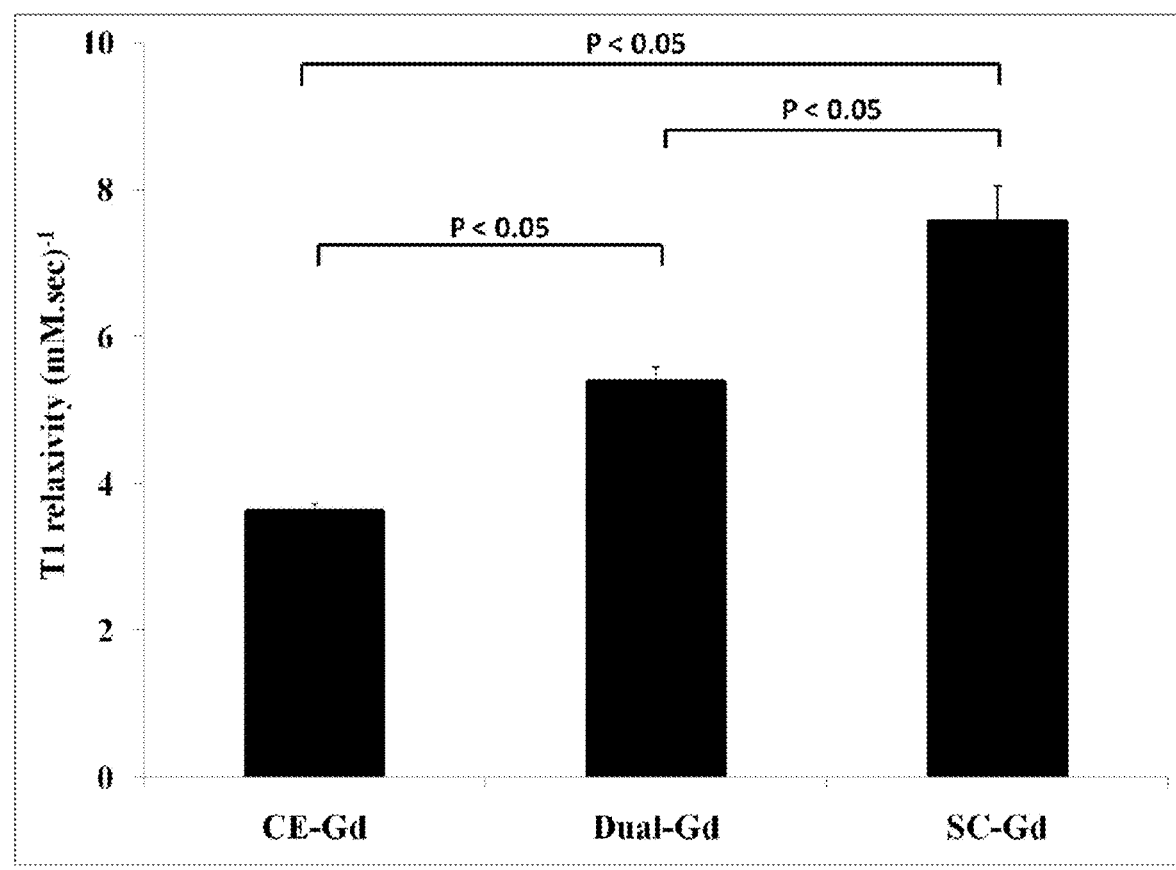
FIG. 2: T1 relaxivity of liposomal-Gd formulations on a per Gadolinium basis. Measurements were performed at 1.5 Tesla MR field strength in bovine plasma at 37° C. Each value is significantly different ($p<0.05$).

The Gd-based molar T1 relaxivities (r1) of the three liposomal formulations were also compared. SC-Gd liposomes demonstrated the highest r1 whereas CE-Gd liposomes had the lowest (FIG. 2). The r1 of Dual-Gd was significantly lower than that of SC-Gd (p<0.05). The higher r1 observed for SC-Gd is a result of more liposomal particles present per unit concentration of Gd. Consequently, more Gd atoms are exposed to the bulk water molecules which eventually results in an enhanced T1 relaxation effect. No significant changes in the r1 were observed over a one week period.

Figure 3:
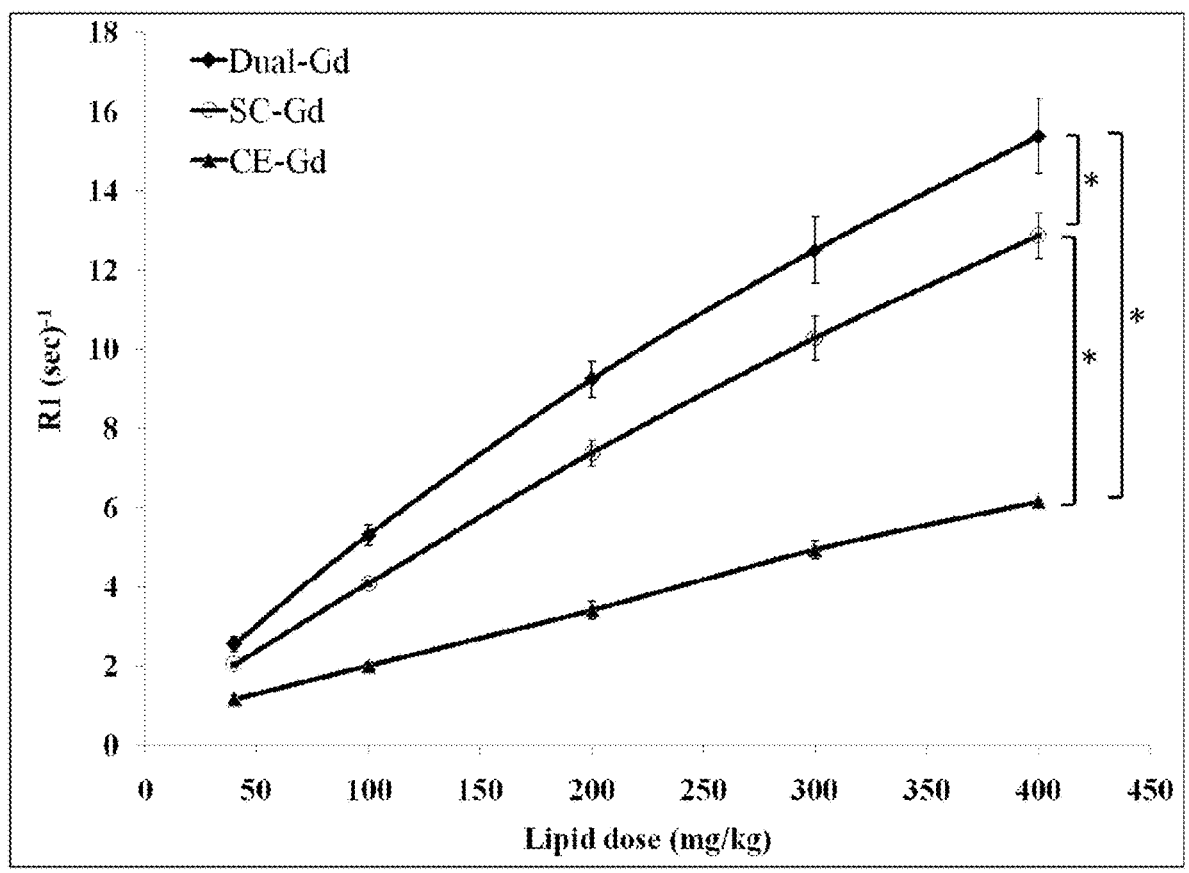
FIG. 3: T1 relaxation rates (R1) of liposomal-Gd formulations for different lipid doses. Measurements were performed at 1.5 Tesla MR field strength in bovine plasma at 37° C. For each lipid dose, the R1 values were significantly different for each of the liposomal-Gd agent (* corresponds to $p<0.05$).
Figure 4:
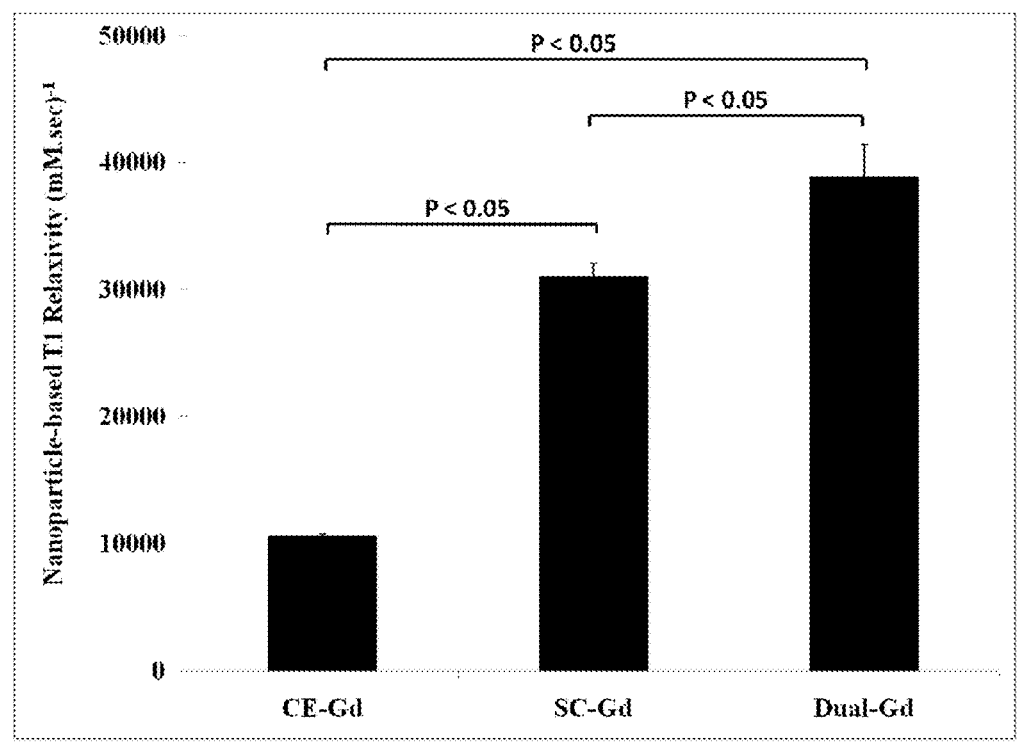
FIG. 4: T1 relaxivity of liposomal-Gd formulations on a per nanoparticle basis.

To compare the relaxation properties of liposomal formulations on a particle basis, in vitro T1 relaxation rates (R1) were measured for diluted samples prepared in bovine plasma. The dilutions were performed on a lipid-dose basis i.e., amount of lipid administered (mg) per unit of body weight (kg). The Dual-Gd and SC-Gd liposomes had at least two-fold higher relaxation rates compared to CE-Gd liposomes at all lipid doses (p<0.05, FIG. 3). The Dual-Gd liposomes demonstrated the highest R1 on a particle-basis among the three formulations (p<0.05 Dual-Gd vs SC-Gd, FIG. 2). The higher R1 for Dual-Gd liposomes is a combined effect of surface-conjugated and core-encapsulated gadolinium which causes more protons to relax compared to either SC-Gd or CE-Gd liposomes. This is also evident in the T1 relaxivities calculated on a nanoparticle-basis (FIG. 4). Dual-Gd liposomes demonstrated the highest nanoparticle-based T1 relaxivity. The nanoparticle-based T1 relaxivities were more than three orders of magnitude (2000-8000) higher than conventional low molecular-weight contrast agents such as Gd-DTPA. The high T1 relaxivities is a result of their ability to carry several thousands of Gd-chelates per nanoparticle.

Figure 5:
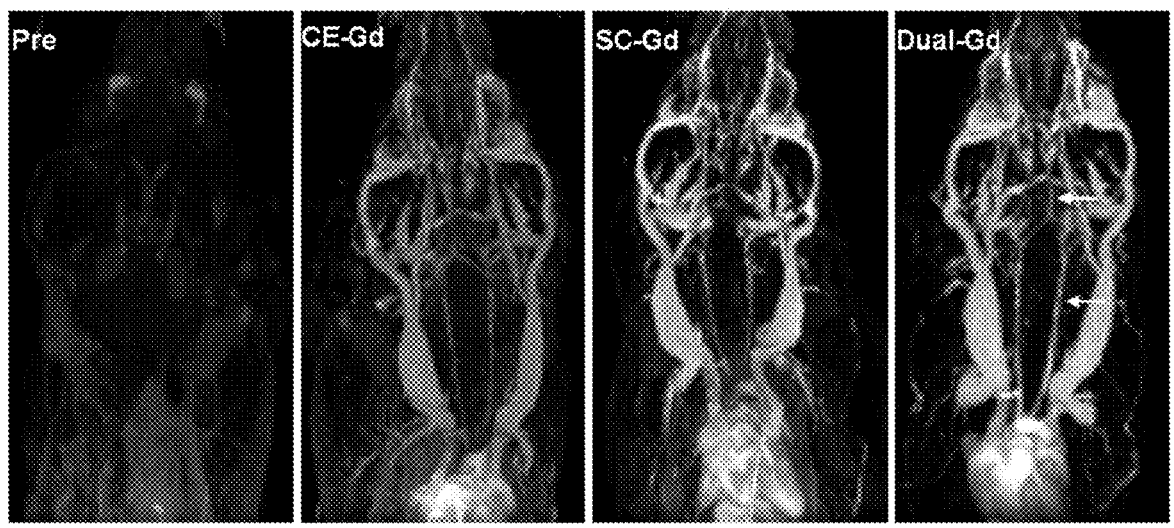
FIG. 5: In vivo comparison of liposomal-Gd contrast agents. Coronal maximum intensity projection (MIP) images of the head and thorax in mice acquired pre-contrast, post CE-Gd liposomes, post SC-Gd liposomes and post Dual-Gd liposomes. The contrast agents were administered intravenously at a lipid dose of 200 mg/kg. Please note the increased signals in the vessels compared to background and the high vessel conspicuity for smaller vessels (arrows in the Dual-Gd image). All images were acquired in different animals using the 3D-FSPGR sequence. The MIP images are presented at identical gray-scale levels.

To compare different liposomal formulations in vivo, the agents were administered at identical lipid dose i.e., resulting in equivalent liposome concentration in the blood. For comparison purposes, all maximum intensity projection (MIP) images were processed to identical brightness/contrast levels. All three agents demonstrated visualization of major vascular features. However, Dual-Gd and SC-Gd liposomes even demonstrated excellent visualization of small vessel features as seen in the coronal MIP images (FIG. 5). Increased signal and relatively lower background were noted in the Dual-Gd images, in addition, smaller vessels became more conspicuous. This is reflected in the SNR and CNR values (FIG. 6), which show that Dual-Gd had the highest SNR and CNR, followed by SC-Gd, and then CE-Gd. The differences in SNR and CNR values for all three agents were statistically significant (p<0.05). The better demonstration of vascular features by Dual-Gd, relative to the other two agents, is a result of higher signal per nanoparticle.

The inventors have demonstrated a new nanoparticle-based Gd agent for T1-weighted MR imaging. The new agent, named Dual-Gd liposomal agent, combines features of two previously described agents, CE-Gd (core-encapsulated Gd liposome) and SC-Gd (surface-conjugated Gd liposome) to create a new entity that is capable of delivering a higher concentration of Gd, and greater signal enhancement per particle. Upon in vivo imaging, the Dual-Gd resulted in both improved SNR and CNR. Among other applications, the agent should find use in vascular imaging, particularly for evaluation of small features that can be critical for clinical decision making and for imaging of small animals; as well as, in molecular imaging, where the number of imaging agents per particle bound to the target is critical for creating sufficient signal for target identification.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Anzalone et al., Eur. Radiol., 16(Suppl 7):M27-34, 2006.
Ayyagari et al., Magn. Reson. Med., 55:1023-9, 2006.
Bremerich et al., Eur. Radiol., 17:3017-24, 2007.
Bucholz et al., Magn. Reson. Med., 60:111-8, 2008.
Choyke et al., J. Magn. Reson. Imaging, 17:509-20, 2003.
Eckelman, Drug Discov. Today, 8:404-410, 2003.
Ferrari, Nature Rev., 5:161-171, 2005.
Frias et al., J. Am. Chem. Soc., 22:16316-7, 2004.
Gabizon et al., Clin. Pharmacokinet., 42:419-36, 2003.
Ghaghada et al., Acad. Radiol., 15:1259-63, 2008.
Ghaghada et al., AJNR 2007; 28: 48-53, 2007.
Ghaghada et al., J. Control Release, 104:113-28, 2005.
Gupta et al., Biomaterials, 26:3995-4021, 2005.

Hadizadeh et al., *Radiology*, 249:701-11, 2008.
Immordino et al. *Int. J. Nanomedicine*, 1(3):297-315, 2006.
Ishida et al., *Int. J. Pharm.*, 190:49-56, 1999.
Kamaly and Miller, *Int. J. Mol. Sci.*, 11(4):1759-76, 2010.
Karathanasis et al., *PLoS One*, 4:e5843, 2009.
Knopp et al., *J. Magn. Reson. Imaging*, 17:694-702, 2003.
Kobayashi and Brechbiel, *Adv. Drug Deliv. Rev.*, 57:2271-86, 2005.
McNeeley et al., *Biomaterial*, 30:3986-3995, 2009.
Mulder et al., *Bioconjug. Chem.*, 15:799-806, 2004.
Port et al., *Invest. Radiol.*, 40:565-73, 2005.
Rosen and Schnall, *Clin. Cancer Res.*, 13:770s-776s, 2007.
Saul et al., *J. Control Release*, 92:49-67, 2003.
Scheinin et al., *J. Ann. Med.*, 31:430-431, 1999.
Storrs et al., *J. Magn. Reson. Imaging*, 5:719-24, 1995.
Szebeni, *Toxicology*, 216:106-21, 2005.
Terreno et al., *Magn. Reson. Med.*, 55(3):491-7, 2006.
Tilcock et al., *Radiology*, 171:77-80, 1989.
Tran et al., *Int. J. Nanomedicine*, 2:515-26, 2007.
Welch et al., *J. Nucl. Med.*, 50:1743-1746, 2009.
Winter et al., *Magn. Reson. Med.*, 50:411-6, 2003.
Zhang et al., *J. Magn. Reson. Imaging*, 25:13-25, 2007.

What is claimed is:

1. An imaging nanoparticle comprising a liposome or micelle, wherein the liposome or micelle comprises a first $T_1$ relaxation magnetic resonance imaging agent on the surface of the liposome or micelle and a second $T_1$ relaxation magnetic resonance imaging agent that is encapsulated within the liposome or micelle; wherein the liposome or micelle is formulated for magnetic resonance imaging;
   wherein the nanoparticle comprises the first and second $T_1$ relaxation magnetic resonance imaging agents in an amount that together result in an increase in the $T_1$ relaxivity signal from 0.2 fold to 4 fold on a per nanoparticle basis, wherein the nanoparticle has a diameter of about 10-300 nm when the $T_1$ relaxation signal is measured, and wherein the $T_1$ relaxation signals are obtained by diluting in bovine plasma in vitro;
   wherein the increase in the $T_1$ relaxivity signal on a per nanoparticle basis is relative to a corresponding liposome or micelle that contains either the same amount of the first $T_1$ relaxation magnetic resonance imaging agent on the surface of the liposome or micelle or the same amount of the second $T_1$ relaxation magnetic resonance imaging agent encapsulated within the liposome or micelle;
   wherein the first $T_1$ relaxation magnetic resonance imaging agent is Gd-DTPA bis(stearylamide) (Gd-DTPA-BSA) and
   the second $T_1$ relaxation magnetic resonance imaging agent is gadobenate dimeglumine (Gd-BOPTA)
   wherein the nanoparticle comprises dipalmitoyl-sn-glycero-3-phosphocholine (DPPC), cholesterol, and 1,2-distearoyl-sn-glycero-3-phosphoethanolamine-N-[methoxy(poly(ethylene glycol))-2000] (mPEG2000-DSPE); and
   wherein the nanoparticles have been formed by a method comprising mixing in ethanol, rehydrating, and extruding through a filter or membrane, wherein the filter or membrane has a plurality of openings about 10-400 nm in size; and
   wherein the rehydrating comprises exposing the nanoparticle to a solution comprising the second $T_1$ relaxation magnetic resonance imaging agent.

2. The nanoparticle of claim 1, wherein the nanoparticle further comprises a surface stabilizer, wherein surface stabilizer is selected from the group consisting of citrate, cysteine, folic acid, polyacetylene glycol, polypropylene glycol, copolymers of polyethylene glycol and polypropylene glycol, polylysine, polyvinyl alcohol, human serum albumin, bovine serum albumin, hyaluranic acid, polyethyleimine (PEI), polyvinylprrolidone (PVP), and polyethylene glycol (PEG).

3. The nanoparticle of claim 1, wherein the nanoparticle further comprises a radioisotope.

4. The nanoparticle of claim 1, wherein the nanoparticle further comprises a light-based imaging agent, a nuclear medicine imaging agent, a CT imaging agent, an ultrasound imaging agent, or a photoacoustic imaging agent.

5. The nanoparticle of claim 1, wherein the nanoparticle further comprises a chemotherapeutic.

6. The nanoparticle of claim 1, wherein the nanoparticle comprises a third imaging agent.

7. The nanoparticle of claim 1, wherein the nanoparticle is further coupled with a targeting moiety, a tumor targeting moiety, a targeting ligand, a therapeutic, a peptide, an antibody, a nucleic acid, a small molecule, or a polymer.

8. The nanoparticle of claim 7, wherein the targeting ligand binds to CD44, binds to folate receptors, or targets a somatostatin receptor.

9. The nanoparticle of claim 8, wherein the targeting ligand comprises hyaluronic acid (HA) or folic acid.

10. The nanoparticle of claim 7, wherein the tumor targeting moiety targets somatostatin receptor type 2.

11. The nanoparticle of claim 7, wherein the tumor targeting moiety comprises octreotide.

12. A method of imaging a subject comprising administering a nanoparticle of claim 1 to a subject and imaging at least a portion of the subject with magnetic resonance imaging.

13. The method of claim 12, wherein the administering comprises intravenous administration, intracardiac administration, intradermal administration, intralesional administration, intrathecal administration, intracranial administration, intrapericardial administration, intraumbilical administration, intraocular administration, intraarterial administration, intraperitoneal administration, intraosseous administration, intrahemmorhage administration, intratrauma administration, intratumor administration, subcutaneous administration, intramuscular administration, intravitreous administration, direct injection into a normal tissue, or direct injection into a tumor.

14. The method of claim 13, wherein the method further comprises imaging a tumor in the subject.

15. The method of claim 12, wherein the method further comprises a method of imaging atherosclerosis or an atherosclerotic plaque.

16. The method of claim 12, wherein the subject is a human.

17. A method of imaging and treating an angiogenic or a malignant tissue in a subject, comprising administering to a subject an effective amount of a nanoparticle of claim 1 to a subject, wherein the nanoparticle further comprises a therapeutic agent subject, and imaging at least a portion of the subject with magnetic resonance imaging.

18. The method of claim 17, wherein the therapeutic agent is an anticancer agent.

19. The method of claim 18, wherein the anticancer agent is a chemotherapeutic, radioisotope, phototherapeutic, therapeutic RNA, an siRNA, or a gene therapy.

20. The method of claim 19, wherein the anticancer agent is a chemotherapeutic, and wherein the chemotherapeutic is doxorubicin.

21. The method of claim 17, wherein the mammal is a human.

22. The nanoparticle of claim 4, wherein the light-based imaging agent is a visible light imaging agent, a near-infrared light (NIR) imaging agent, or an infrared light (IR) imaging agent.

23. The nanoparticle of claim 22, wherein the light-based imaging agent is a cyanine.

24. The nanoparticle of claim 1, wherein the first $T_1$ relaxation magnetic resonance imaging agent is covalently bound to a surface moiety, wherein the surface moiety is associated with the surface of the nanoparticle and the surface moiety further comprises a surface stabilizer.

25. The nanoparticle of claim 1, wherein the extruding comprises passing through three distinct filters or membranes.

26. The nanoparticles of claim 1, wherein the filter or membrane has a plurality of openings about 100-200 nm in size.

27. The nanoparticle of claim 1, wherein the nanoparticle exhibits a T1 relaxivity that is from about two-fold to about 2.5-fold higher than the T1 relaxivity of a corresponding liposome or micelle that contains the same amount of the second $T_1$ relaxation magnetic resonance imaging agent encapsulated within the liposome or micelle but that does not contain the $T_1$ relaxation magnetic resonance imaging agent on the surface of the liposome, wherein the relaxivity (R1) of the corresponding liposome or micelle is greater than 4 $sec^{-1}$ at a lipid dose of 400 mg/kg.

28. The nanoparticle of claim 27, wherein the nanoparticle is comprised in an aqueous solution.

29. The nanoparticle of claim 27, wherein the rehydrating further comprises heating the solution.

30. The nanoparticle of claim 29, wherein the heating comprises heating to about 60° C.

31. The nanoparticles of claim 25, wherein the three distinct filters or membranes each have a plurality of openings about 100-400 nm in size.

32. The nanoparticle of claim 25, wherein the three distinct filters or membranes having a plurality of openings about 100-400 nm in size.

33. The nanoparticle of claim 1, wherein the nanoparticles comprise DPPC, Gd-DTPA-BSA, Cholesterol, and mPEG2000-DSPE at a molar ratio of about 30:25:40:5.

* * * * *